United States Patent
Hilton et al.

(10) Patent No.: US 9,226,955 B2
(45) Date of Patent: Jan. 5, 2016

(54) ALLOGENEIC AUTOPHAGOSOME-ENRICHED COMPOSITION FOR THE TREATMENT OF DISEASE

(71) Applicants: UbiVac, LLC, Portland, OR (US); Providence Health & Services-Oregon, Portland, OR (US)

(72) Inventors: Traci Hilton, Portland, OR (US); Sandra Aung, Solana Beach, CA (US); Rieneke van de Ven, The Hague (NL); Christopher Paustian, Portland, OR (US); Tarsem Moudgil, Beaverton, OR (US); Christopher Dubay, Portland, OR (US); Christopher Twitty, Solana Beach, CA (US); Hong-Ming Hu, Portland, OR (US); Bernard A. Fox, Portland, OR (US)

(73) Assignees: UbiVac, LLC, Portland, OR (US); Providence Health & Services-Oregon, Portland, OR (US)

(*) Notice: Subject to any disclaimer, the term of this patent is extended or adjusted under 35 U.S.C. 154(b) by 0 days.

(21) Appl. No.: 14/061,135

(22) Filed: Oct. 23, 2013

(65) Prior Publication Data

US 2014/0112977 A1    Apr. 24, 2014

Related U.S. Application Data

(60) Provisional application No. 61/717,585, filed on Oct. 23, 2012.

(51) Int. Cl.
*A61K 39/39* (2006.01)
*A61K 39/00* (2006.01)
*G01N 33/50* (2006.01)

(52) U.S. Cl.
CPC ............. *A61K 39/0011* (2013.01); *A61K 39/39* (2013.01); *G01N 33/505* (2013.01); *G01N 33/5047* (2013.01); *A61K 2039/55522* (2013.01); *A61K 2039/55561* (2013.01)

(58) Field of Classification Search
CPC .................. A61K 39/0011; A61K 2039/5154; A61K 2300/00; A61K 2039/55522; A61K 39/39; A61K 45/06; A61K 2039/5158; A61K 2039/55561; A61K 2039/55555
See application file for complete search history.

(56) References Cited

U.S. PATENT DOCUMENTS

| | | | |
|---|---|---|---|
| 2007/0128207 A1 | 6/2007 | Sugiyama | |
| 2009/0220530 A1 | 9/2009 | Hu | |
| 2009/0317407 A1* | 12/2009 | LaCelle et al. | 424/174.1 |
| 2010/0316667 A1* | 12/2010 | Diamond et al. | 424/199.1 |

FOREIGN PATENT DOCUMENTS

WO    2012139094 A2    10/2012

OTHER PUBLICATIONS

Twitty, Christopher G., et al. "Tumor-Derived Autophagosome Vaccine: Induction of Cross-Protective Immune Responses Against Short-Lived Proteins through a p62-Dependent Mechanism." Clinical Cancer Research, vol. 17, No. 20, Aug. 2, 2011, pp. 6467-6481.
Rosenberg, Steven A. et al., "Cancer Immunotherapy: Moving Beyond Current Vaccines", Nature Medicine vol. 10, No. 9, Sep. 2004, pp. 909-915.
Paustian, Christopher, "Autophagosome-enriched Cancer Vaccine Strategy Provides a Novel Non-genetic Method to Engineer Leukocytes to Express Molecules that may Augment Cancer Immunotherapy", AAI 2013: American Association of Immunologists Annual Meeting, May 2013, 44 pages.
Cheever, Martin A., et al. "The Prioritization of Cancer Antigens: a National Cancer Institute Pilot Project for the Acceleration of Translational Research", Clinical Cancer Research vol. 15, No. 17, Sep. 1, 2009, pp. 5323-5337.
Hilton, Traci L., et al., "A Novel Autophagosome Cancer Vaccine Derived from Non-Small Cell Lung Cancer (NSCLC) contains at least six NCI prioritized Cancer Antigens and Ligands for TLR 2, 3, 4, 7 and 9.", SITC 2012: Society for Immunotherapy of Cancer Annual Meeting, Oct. 2012, 1 page.
Li, Yuhuan, et al. "Tumor-Derived Autophagosome Vaccine: Mechanism of Cross-Presentation and Therapeutic Efficacy", Clinical Cancer Research vol. 17, No. 22, Nov. 15, 2011, pp. 7047-7057.
Kanzler, Holger, et al. "Therapeutic Targeting of Innate Immunity with Toll-like Receptor Agonists and Antagonists", Nature Medicine vol. 13, No. 5, May 2007, pp. 552-559.
ISA Korean Intellectual Property Office, International Search Report and Written Opinion of PCT/US2013/066391, Dec. 20, 2013, WIPO, 6 pages.

* cited by examiner

*Primary Examiner* — Daniel C Gamett
(74) *Attorney, Agent, or Firm* — Alleman Hall McCoy Russell & Tuttle LLP

(57) ABSTRACT

A composition, comprising: an enriched population of autophagosomes derived from a non-small cell lung carcinoma cell line, and wherein the enriched population of autophagosomes includes: one or more toll-like receptor agonists; one or more tumor antigens; and one or more damage-associated molecular pattern molecules. In this way, an off-the-shelf vaccine may be available to be administered in order to stimulate a targeted immune response in patients bearing different tumor types.

17 Claims, 25 Drawing Sheets

| Antigens | LT3 Expression | LT6 Expression | Normal Lung |
|---|---|---|---|
| 1. WT1 | 207.8 | 250.9 | 132.5 |
| 2. MP2 | 453.2 | 495.6 | 1173.4 |
| 5. EGFRvIII (EGFR) | 2488.1 | 1315 | 1088.6 |
| 6. HER-2/neu | 457.3 | 182.1 | 822.6 |
| 9. p53 nonmutant (TP53) | 1645.6 | 2778.5 | 1109.9 |
| 12. GD2 (B4GALNT1) | 1377 | 859.8 | 66 |
| 15. Ras mutant | | | |
| (KRAS) | 553.5 | 1450.5 | 225 |
| (HRAS) | 622.1 | 618.5 | 466 |
| (MRAS) | 1295.8 | 163.2 | 505.7 |
| (NRAS) | 3498.4 | 3281 | 1912.7 |
| 17. p53 mutant (TP53) | 1645.6 | 2778.5 | 1109.9 |
| 21. Survivin | 247.8 | 552.5 | 148.6 |
| 25. EphA2 | 1410.4 | 1835.7 | 315.6 |
| 29. EpCAM | 30.6 | 427.6 | 983.5 |
| 31. NA17 (MGAT5) | 1348.9 | 849.5 | 531.1 |
| 32. PAX3 | 243.2 | 28.8 | 24.9 |
| 34. Androgen receptor | 43.7 | 210.7 | 155.8 |
| 35. Cyclin B1 | 422.1 | 1143 | 57.1 |
| 38. RhoC | 3341.8 | 4018.7 | 3570.4 |
| 42. Mesothelin | 994.8 | 170.1 | 1583.2 |
| 53. NY-BR-1 | 312.4 | 18.4 | 12 |
| 55. SART3 | 811 | 786.7 | 354.3 |
| 60. Sperm protein 17 | 534.1 | 416.6 | 225.7 |
| 65. XAGE 1 (XAGE1D) | 75.7 | 2192.9 | 66 |
| 66. B7H3 | 632.8 | 1136.6 | 497 |
| 67. Legumain | 3463.5 | 5832.5 | 4774.3 |
| 73. PDGFR-β | 512 | 165.7 | 1968.3 |
| 75. Fos-related antigen | 2773.5 | 2936.7 | 273.9 |

FIG. 3A  FIG. 3B

| NCI Prioritized Antigens | Gene Expression | | Flow | Protein Detection Method | | |
|---|---|---|---|---|---|---|
| | UbiLT3 | UbiLT6 | | Mass Spec | Western Blot | |
| | | | | | UbiLT3 | UbiLT6 |
| WT1 | 1.6 | 1.9 | | | ▬ | ▬ |
| EGFRvIII | 2.3 | 1.2 | X | X | | |
| HER-2/neu | 0.6 | 0.2 | X | | | |
| P53 | 1.5 | 2.5 | | | ▬ | ▬ |
| Survivin | 1.7 | 3.7 | X | | | ▬ |
| EphA2 | 4.5 | 5.8 | X | X | ▬ | ▬ |
| Cyclin B1 | 7.4 | 20 | | | ▬ | ▬ |
| XAGE 1 | Nd | 33.2 | | | | ▬ |
| PDGFR-β | 0.3 | nd | | X | ▬ | ▬ |

| Gene Name | UbiLT3 | UbiLT6 | Detection Method | | |
|---|---|---|---|---|---|
| | | | Aria / Flow | Western | Mass Spec |
| BIRC5 | 247.8 | 552.5 | YES | YES | |
| CCNB1 | 422.1 | 1143.0 | | YES | |
| CPSF1 | 653.1 | 949.3 | | | YES |
| EGFR | 2488.1 | 1315.0 | YES viii | | YES |
| EPHA2 | 1410.4 | 1835.7 | YES | | YES |
| ERBB2 | 457.3 | 182.1 | YES | YES | |
| FMNL1 | 390.7 | 479.6 | | | YES |
| PPIB | 7846.3 | 8266.2 | | | YES |
| RAB38 | 92.1 | 171.5 | | | YES |
| TOP2A;TOP2B | 696.6 | 2499.3 | | | YES |
| TP53 | 1645.6 | 2778.5 | | | |
| WT1 | 207.8 | 250.9 | | YES | |
| XAGE1 | 75.7 | 2192.9 | | YES | |
| PDGFR-β | 512 | 1968.3 | | YES | YES |
| ANXA2 | 6767.0 | 7254.2 | | | YES |
| ATIC | 1492.5 | 1857.3 | | | YES |
| BCAP31 | 3178.0 | 3438.8 | | | YES |
| HNRPL | 2412.3 | 3804.5 | | | YES |
| IGF2BP3 | 1043.6 | 1128.7 | | | YES |
| MFI2 | 998.2 | 490.9 | | | YES |
| PA2G4 (Ebp1) | 6780.6 | 6671.1 | | | YES |
| PGK1 | 7270.3 | 6070.1 | | | YES |
| RPSA | 3162.8 | 3313.9 | | | YES |
| SEPT2' | 3511.6 | 3974.1 | | | YES |
| ENO1 | 9815.9 | 12120.8 | | YES | YES |
| KPNA2 | 6769.8 | 7694.4 | | YES | YES |
| PKM2 | 7364.6 | 9544.8 | | YES | YES |
| LDHB | 9971.5 | 12151.9 | | YES | YES |

FIG. 3E

| GENE | UbLT3 | UbLT6 | Normal Lung |
|---|---|---|---|
| HMGB1 | 1975.9 | 2640.0 | 1671.7 |
| HSPA1A | 18567.6 | 19513.7 | 6913.5 |
| HSPA4 | 3959.8 | 3452.9 | 270.7 |
| HSP90AB1 | 12916.3 | 14171.5 | 5005.5 |
| HSP90AA1 | 10925.4 | 11767.3 | 1688.1 |
| HSP90AA2 | 2046.6 | 2794.9 | 504.6 |
| HSP90B1 | 9235.7 | 11925.0 | 2760.7 |
| HDGF | 5586.0 | 4790.0 | 2482.0 |
| IL1A | 1330.6 | 98.8 | 60.0 |
| LGALS8 | 1987.4 | 1654.5 | 790.4 |
| Nucleolin | 2440.2 | 3415.3 | 850.5 |
| ANXA5 | 8806.2 | 11317.0 | 5783.4 |
| ANXA1 | 11411.5 | 15201.2 | 5817.6 |

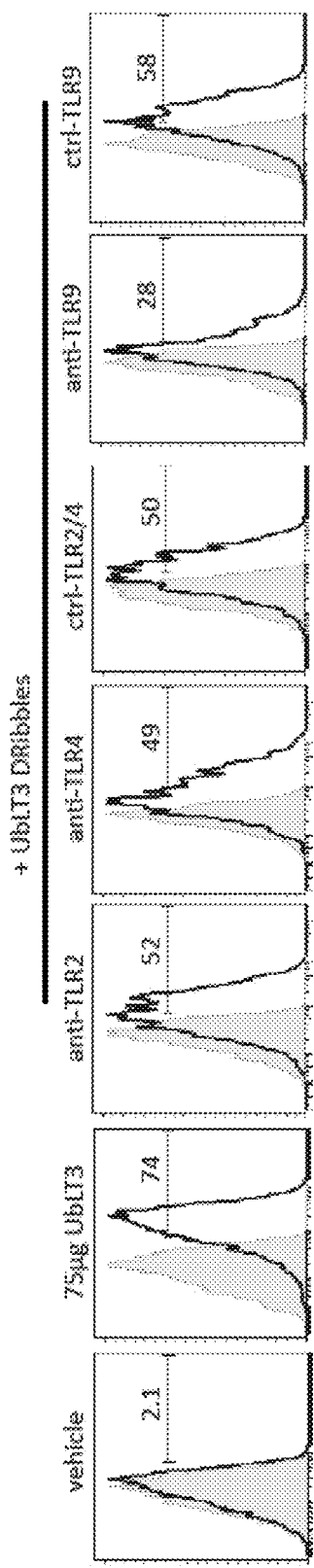
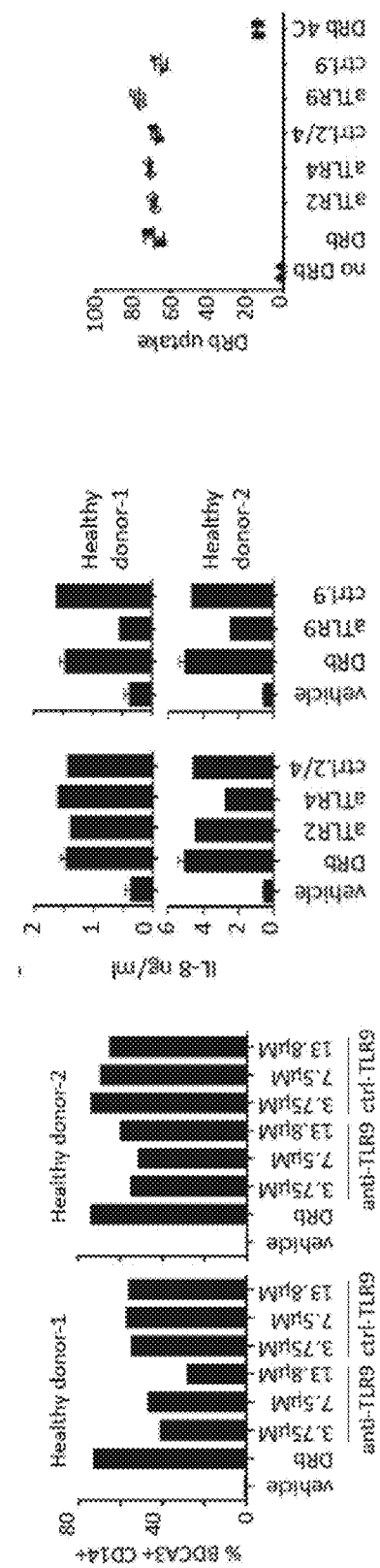
FIG. 9A
FIG. 9B
FIG. 9C
FIG. 9D

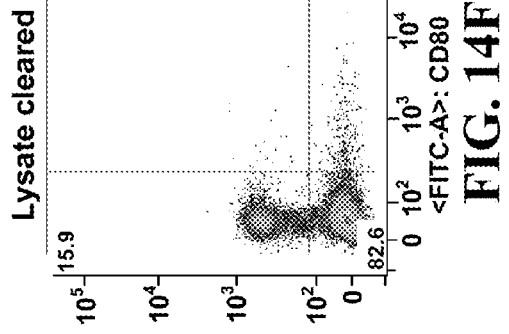
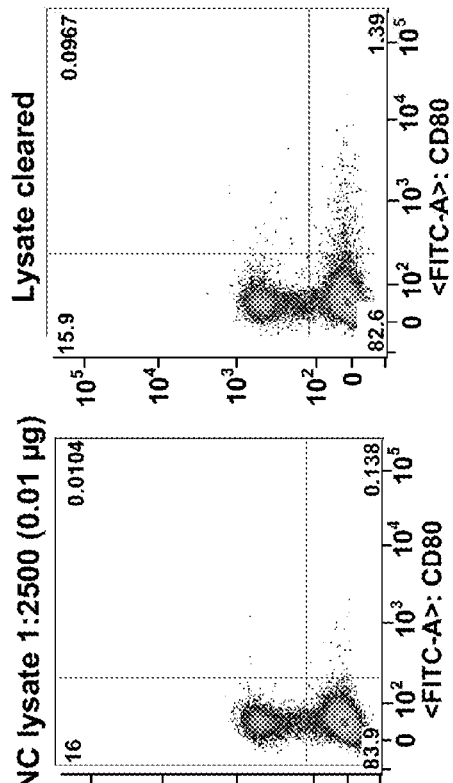
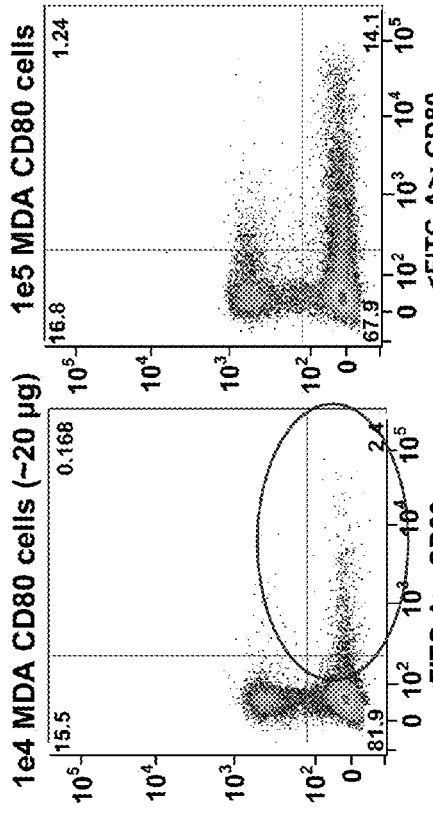
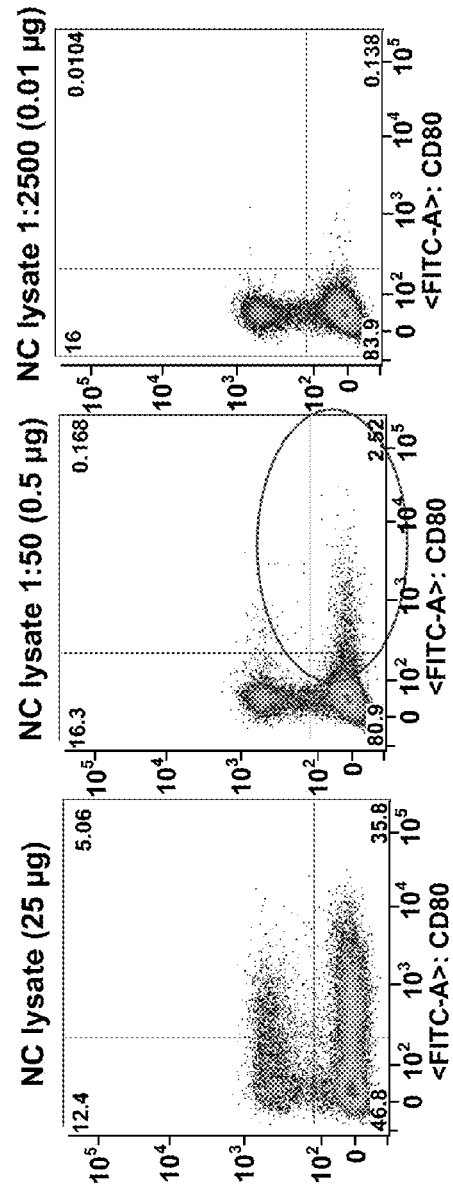

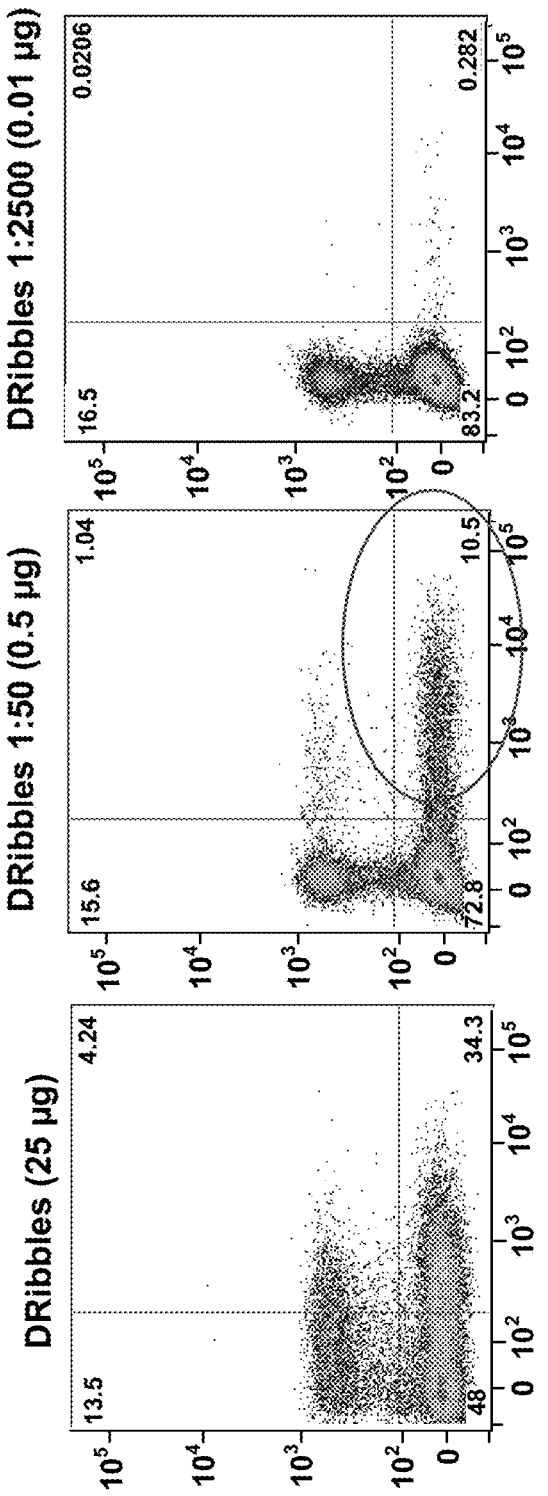

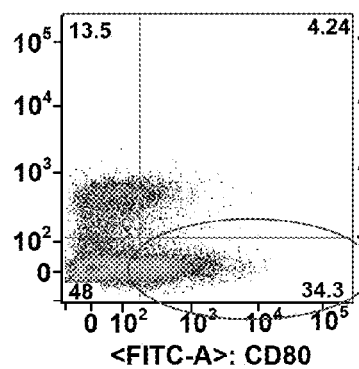
FIG. 15A Mouse SOP, supernatant/wash DRibbles
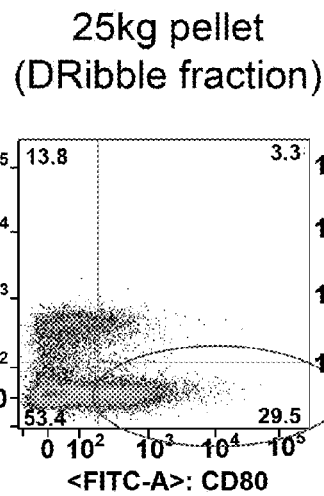
FIG. 15B 25kg pellet (DRibble fraction)
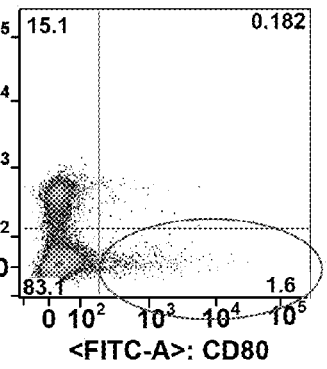
FIG. 15C 12k xg sup. (putative exosome fraction)
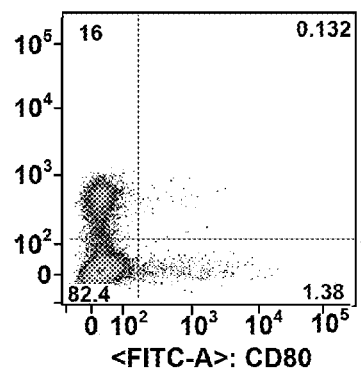
FIG. 15D 25k xg sup.
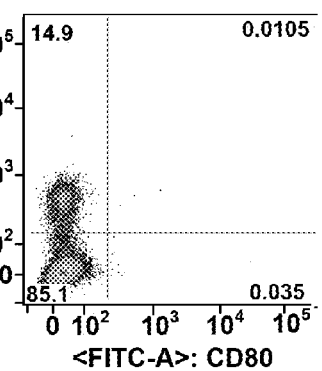
FIG. 15E untreated

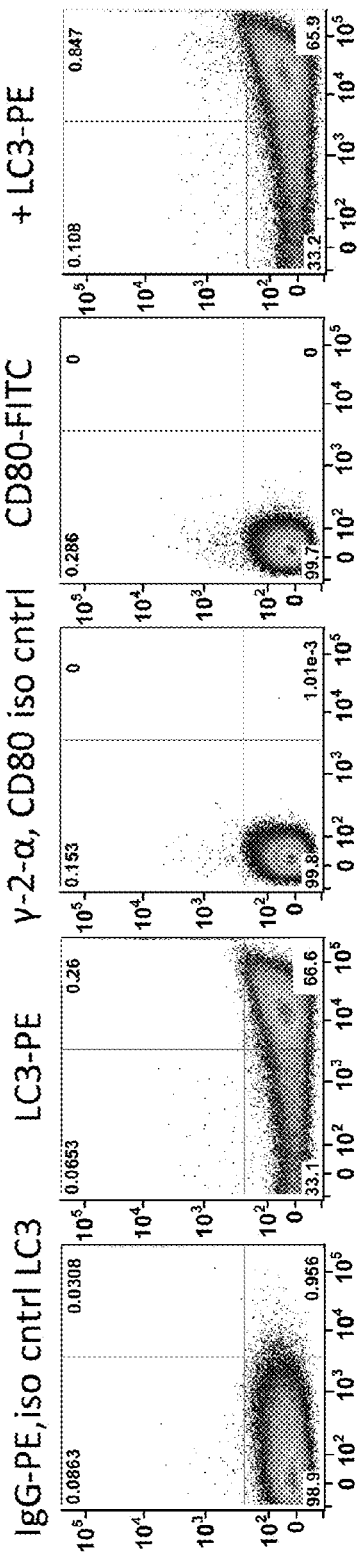
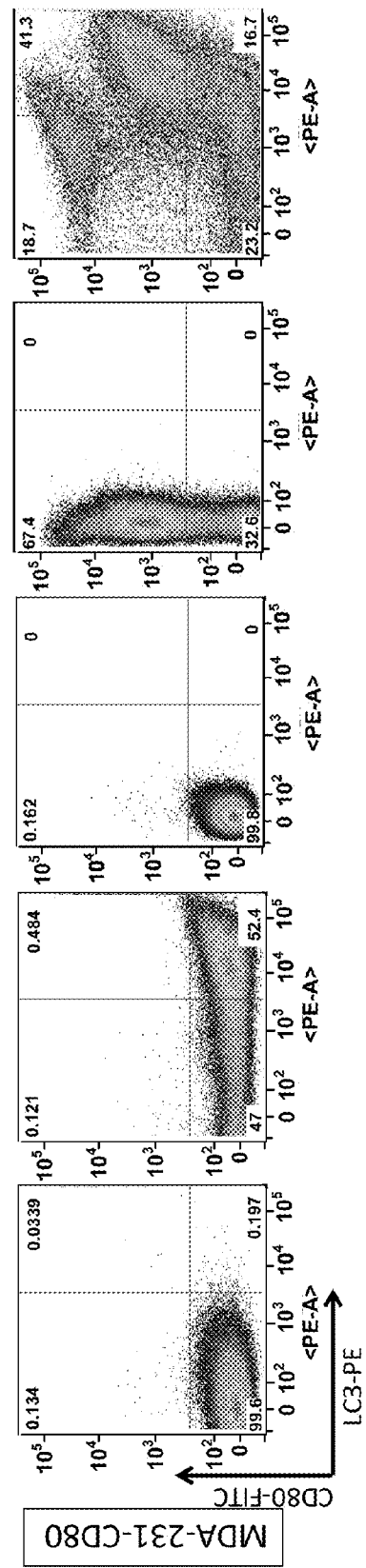
FIG. 16A FIG. 16B FIG. 16C FIG. 16D FIG. 16E
FIG. 16F FIG. 16G FIG. 16H FIG. 16I FIG. 16J

ALLOGENEIC AUTOPHAGOSOME-ENRICHED COMPOSITION FOR THE TREATMENT OF DISEASE

CROSS REFERENCE TO RELATED APPLICATION

This application claims priority to U.S. Provisional Patent Application No. 61/717,585, filed Oct. 23, 2012, entitled "AUTOPHAGOSOME-ENRICHED COMPOSITION FOR THE TREATMENT OF DISEASE", the entire contents of which are hereby incorporated herein by reference for all purposes.

FIELD

This application relates to autophagosome-enriched compositions and methods of stimulating, enhancing or facilitating an immune response by administration of autophagosome-enriched product on their own or in conjunction with complementary therapeutics.

BACKGROUND AND SUMMARY

Cross-presentation of exogenous antigens by host professional antigen-presenting cells (APCs) plays a pivotal role in the initiation and development of T-cell immune responses to tumor associated antigens, including self or mutated self-antigens derived from tumor cells, and foreign antigens derived from infectious agents. Prospective cancer vaccines have been developed that attempt to harness the cross-presentation of exogenous antigens to illicit a specific immune response against a tumor.

However, specific active immunization with cancer vaccines has not been very effective in animal models or in clinical trials (Rosenberg et al., Nat. Med. 10:909-15, 2004.). The primary obstacle to the success of cancer immunotherapy has been the inability of the vaccine to induce a large initial expansion and then persistence of tumor-reactive CTL (Rosenberg et al., Nat. Med. 10:909-15, 2004). Another obstacle to currently available methods of cancer immunotherapy is that potential tumor rejection antigens are not known for most cancers, with the exception of melanoma, and the dominant tumor rejection antigens are likely tumor or patient-specific.

Previously, the inventors have determined that reducing or inhibiting cellular protein degradation with a proteasome inhibitor may result in cellular accumulation and secretion of defective ribosomal products (DRiPs) and short lived proteins (SLiPs) (as well as immunogenic fragments thereof) into "blebs". It is shown herein that DRibbles released from, or contained within, cells (such as tumor or pathogen infected cells) after proteasome inhibitor-induced autophagy may accumulate DRiPs and SLiPs (and fragments thereof) in autophagy bodies and induce a strong immunity (such as anti-tumor or anti-pathogen) via cross-priming. For example, tumor-derived DRibbles, as well as Antigen Presenting Cells (APCs) (such as dendritic cells) loaded with tumor-derived DRibbles, may activate tumor-reactive Cytotoxic T-Lymphocytes (CTL) and Helper T-Lymphocytes (HTL) more efficiently than APCs incubated with live or killed tumor cells, both in vitro and in vivo. In particular examples, administration of DRibbles to a subject (for example as an isolated DRibble population, as a population of cells producing DRibbles, or as DRibble-loaded dendritic cells) increases the generation of CD4 and CD8 cells and promotes the production of inflammatory cytokines or chemokines, such as one or more of IL-6, IL-12, and TNF-α.

The inventors have previously disclosed methods for producing and isolating Dribbles (US 2009/0220530). The method includes contacting the target cell with a sufficient amount of proteasome inhibitor under conditions sufficient for producing DRibbles, such as conditions that substantially inhibit protein degradation in the cell. In some examples, the method further includes contacting the target cell with a sufficient amount of an autophagy inducer before, during or after contacting with the proteasome inhibitor. The cell may also be contacted with one or more agents that decrease glycosylation of proteins. In one example, the cell is contacted with sufficient amounts of a proteasome inhibitor (such as 20 nM Velcade), an autophagy inducer (such as rapamycin or HBSS) and $NH_4Cl$ under conditions sufficient to stimulate production of Dribbles by the cell. In one example, the DRibbles produced under said conditions are harvested by separating said DRibbles from the cell. In one exemplary method, a cell may be contacted with a sufficient amount of a composition that may include a proteasome inhibitor under conditions sufficient to substantially inhibit protein degradation in a cell, for example an incubation of 6-24 hours. The cells may then be incubated under conditions sufficient to induce autophagy in the cell, for example an incubation of 6-24 hours with an autophagy inducer. The resulting cells and DRibbles may then be centrifuged under conditions such that the cells are pelleted while the DRibbles remain in solution. The supernatant containing the DRibbles may then be removed and may then be centrifuged under conditions sufficient to pellet the DRibbles.

However, the inventors herein have recognized that the methods for production and isolation of DRibbles disclosed in the prior art may be insufficient to produce and isolate an enriched population of autophagosomes and their component material to be further utilized as an effective vaccine. The present disclosure describes a novel method for screening cell lines (including both cancer and non-cancer cell lines) that may produce effective vaccines. The cell lines may be characterized as producing autophagosomes that may contain Toll-like receptor (TLR) ligands, damage associated molecular patterns (DAMPs), and molecular chaperones in addition to DRiPs, SLiPs and other tumor antigens when treated with proteasome inhibitors and $NH_4Cl$. Additionally, the cross-presentation of tumor antigens contained within DRibbles may be insufficient to produce an effective immune response against a tumor when presented to a general population of APCs. The present disclosure describes methods for effective cross-presentation of antigen contained within enriched autophagosomes by presenting the enriched autophagosome composition to a specific subset of Dendritic Cells (DCs) that express CLEC9A to produce an efficient immune response.

The inventors herein have recognized the above problems and developed compositions and methods to at least partially address the problems. In one example, a composition, comprising: an enriched population of autophagosomes derived from a non-small cell lung carcinoma cell line, and wherein the enriched population of autophagosomes includes: one or more toll-like receptor agonists; one or more tumor antigens; and one or more damage-associated molecular pattern molecules. In this way, an off-the-shelf vaccine may be available to be administered in order to stimulate a targeted immune response in patients bearing different tumor types.

In another example, a method of inducing a specific immune response in a mammal, comprising: providing a composition comprising: an enriched population of autophagosomes derived from a cell line, the enriched population of autophagosomes including: one or more toll-like receptor agonists; one or more tumor antigens; and one or more damage-associated molecular pattern molecules. In this way, an off-the-shelf vaccine may be administered to patients bearing different tumor types, while supplemented with an inflammation inducing adjuvant derived from the patient's own blood cells.

In yet another example, a method for screening cells that produce allogeneic autophagosome enriched compositions able to induce expression of a selective marker on a subpopulation of peripheral blood mononuclear cells, comprising: contacting a cell with a proteasome inhibitor; contacting the cell with a lysosome inhibitor; harvesting the resulting autophagosomes; determining a molecular signature of the resulting autophagosomes; and selecting cells that divert one or more Toll-like receptor agonist and/or one or more molecular chaperones to the autophagosomes. In this way, toll-like receptor agonists, tumor antigens, and damage-associated molecular pattern molecules may be packaged in an allogeneic autophagosome enriched composition with the ability to illicit a specific immune response against numerous cancer types. Further, when cultured with Peripheral blood mononuclear cells (PBMCs), monocytes, or dendritic cells, the resulting allogeneic autophagosome enriched compositions may induce or upregulate expression of BDCA3, and/or CD80, and further may induce secretion of IL-8 or other cytokine by PBMC.

BRIEF FIGURE DESCRIPTIONS

FIG. 3A is a chart which tabulates the presence of NCI prioritized cancer antigens in AAECs.

FIG. 3B is a digital image showing an SDS-PAGE gel indicating the presence of NCI prioritized cancer antigens in AAECs.

FIG. 3E is a summary table of potential non-mutated antigens contained in AAECs.

FIG. 9A is a cytometry plot displaying data indicating AAEC induced upregulation of BDCA3+ cells is inhibited by TLR antagonists.

FIG. 9B is a graph displaying data from two donors indicating percentage of BDCA3+CD14+ cells after titration of TLR9 antagonists and a control ODN.

FIG. 9C is a graph displaying data from indicating concentration of IL-8 in donor PBMC after multiple treatments.

FIG. 9D is a graph displaying data indicative of the efficiency of AAEC uptake with various co-culture treatments.

FIGS. 14A-I are cytometry plots showing LSR analysis of CD80 expression from donor cells incubated with MDA-CD80 AAECs in various combinations. Red circles highlight that AAECs are more efficient at membrane transfer.

FIGS. 15A-E are cytometry plots showing LSR analysis of CD80 expression from donor cells incubated with various fractions of MDA-CD80 AAECs with and without exosomes. Red circles highlight that exosomes do not appear to be involved in CD80 membrane transfer.

FIGS. 16A-J show aria analysis of an AAEC demonstrating that CD80 is expressed on autophagosomes.

Figure 17A:
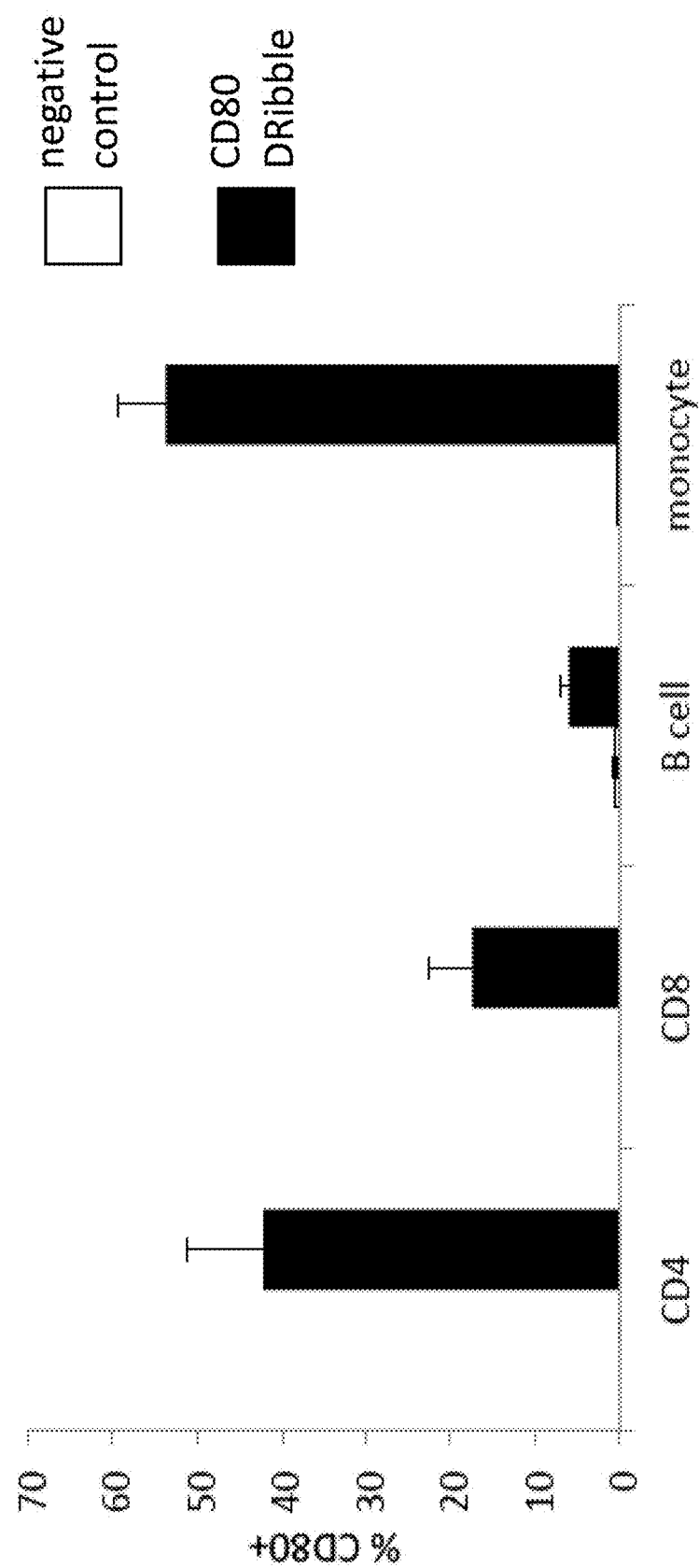

FIG. 17A shows a bar graph demonstrating the transfer of CD80 from an AAEC to various cell types.

Figure 17B:
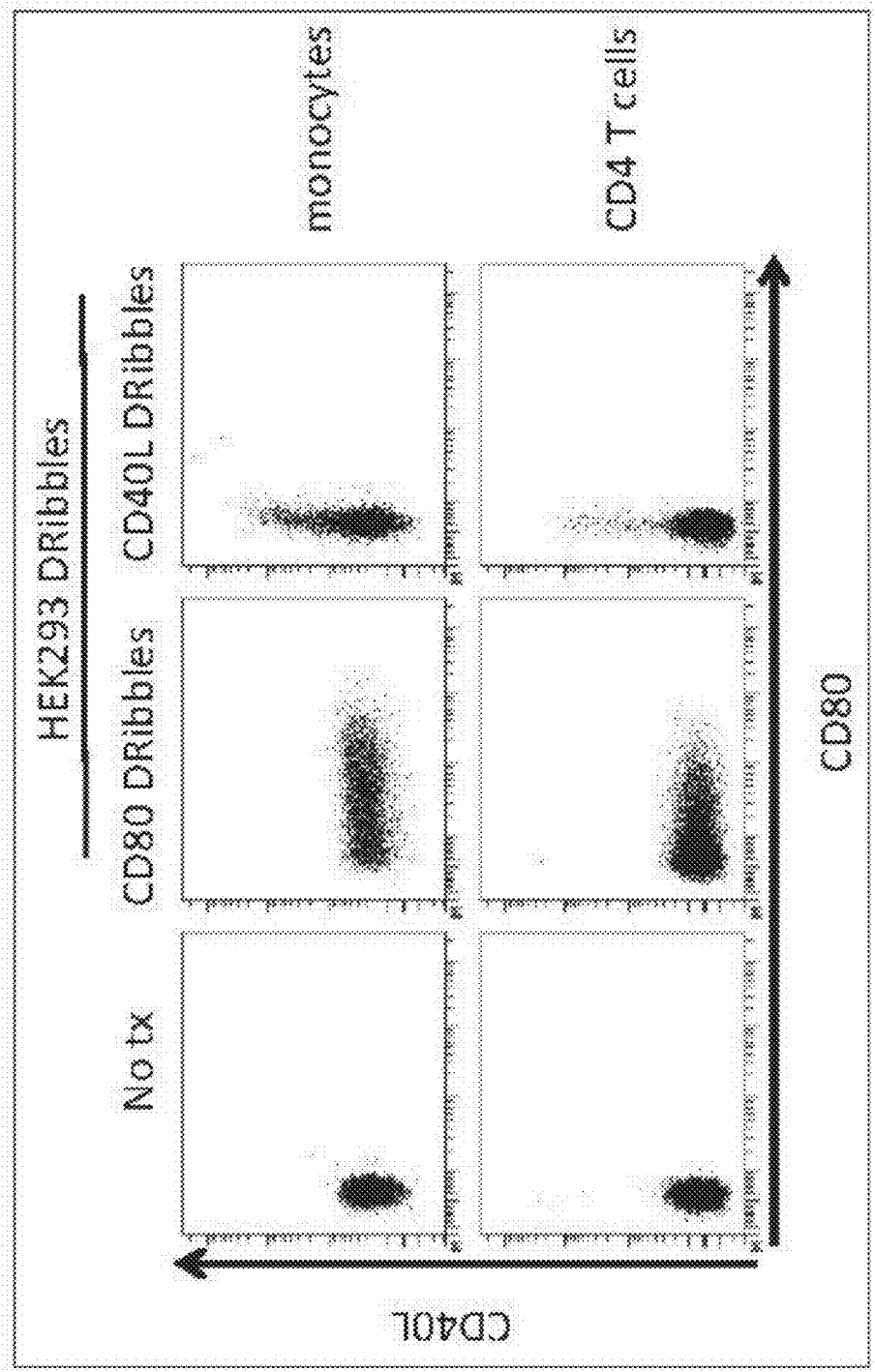

FIG. 17B shows flow cytometry plots demonstrating that AAECs from HEK-293 cells genetically engineered to express CD80 or CD40L can also engage in membrane protein transfer.

DETAILED SPECIFICATION

The present disclosure describes allogeneic autophagosome enriched compositions (AAECs) derived from two Non-Small Cell Lung Carcinoma (NSCLC) tumor cell lines for a Phase I/II clinical trial. These cell lines are herein referred to as UbLT3 (non-specific histopathology) and UbLT6 (adenocarcinoma-like). Below are provided examples of these compositions used to treat murine breast tumors, and to stimulate immune response in peripheral blood mononuclear cells (PBMC) from patients with melanoma, prostate and head and neck squamous cell carcinomas (HNSCC). Additionally, gene profiling indicates and protein analyses confirm that NSCLC cell line derived AAECs contain antigens found in many additional cancers. For example, these cancers may comprise lung; ovarian; sarcoma; colon and rectum adenocarcinoma; and others. One benefit to this broad utility of a single variant of cell-line-derived AAECs is that they may be produced more inexpensively and made to be readily available for treating a variety of cancers increasing their ease of use in patient settings. Though this example embodiment describes the utility of AAECs in cancer vaccines, AAECs may also be used in the treatment of additional, unrelated disease states, to induce an inflammatory response, or as described below, to transfer donor membrane proteins from an autophagosome onto an acceptor cell in a targeted fashion.

DRibble vaccines were described previously as a potential cancer therapeutic that may be derived from tumor cells treated with proteasome and lysosome inhibitors. The present disclosure utilizes a novel method to select cell lines from which to derive an allogeneic autophagosome enriched composition, and also broadens potential applications of the therapy while simplifying composition derivation. Examples provided below include an autophagosome enriched composition derived from NSCLC cell lines. The inventors have demonstrated the presence of myriad antigens that appear in a wide variety of cancer types in the NSCLC derived autophagosome enriched composition. In addition to cancer antigens, the autophagosome enriched composition may contain DAMPs, molecular chaperone proteins, various cytokines, and TLR agonists. These additional components, that may be present in the autophagosome enriched composition, act to preserve antigens so they may be efficiently cross presented as well as capable of augmenting the functional activity of the antigen presenting cell and stimulating an immune response in a patient. Efficient stimulation of an immune response may aid in launching an effective attack on cancerous cells or pathogen-infected cells. Moreover, detailed characterization of the components of autophagosome-enriched compositions allows for further refinement and targeting of the composition for therapeutic goals.

Previous embodiments of the DRibble vaccine envisioned production of vaccine from patient derived tumor cells, or available cancer cell lines of the same type. These vaccines produced promising results in cancers from which the vaccine had been derived. However, some cancer cell types are not readily cultured in vitro and utilizing this prior method, derivation of a vaccine for these cancer types may prove difficult. The present disclosure describes methods for selecting cell or tissue types that are known to culture in vitro and producing compositions or products that may be derived from these cell or tissue types, allowing for a stable composition to be produced without the need for culturing cells derived from a patient biopsy. In some embodiments, the composition may be derived from cells that have been genetically engineered to express additional antigens and/or other additional immunologically reactive molecules. The inventors have recognized that this composition may be implemented as an off-the-shelf vaccine, product, or immunostimulant that may be applicable across a broad range of cancers or infectious diseases.

Although described in regards to a vaccine, it should be appreciated that the disclosure includes methods, compositions and applications of other compositions for treatment of human disease.

In addition to their role as a potential cancer therapeutic for multiple cancer types and histologies, the pro-inflammatory properties of AAECs and other autophagosome enriched compositions are disclosed herein. The inventors have demonstrated that AAECs may comprise TLR-ligands, DAMPs, and various cytokines. These and other molecules that may be contained in AAECs may not serve directly as antigens but, when uptaken by appropriate APCs, may serve a pro-inflammatory purpose by inducing cytokine production and other cellular signals which stimulate an immune response and may lead to effective treatment of diseases which the selected autophagosome enriched composition may target.

The autophagosome enriched composition and its related methods of production and characterization differ compared to present vaccines used for cancer and infectious diseases. For example, the autophagosome enriched composition may incorporate both SLiPs and DRiPs that are typically cross presented inefficiently when cross presented in the absence of an autophagosome. In normal cellular conditions, cross-presentation of these molecules may be inefficient because they are heavily degraded by the proteasome or lysosome. Incorporation of these protein products into an autophagosome creates an environment in which they are efficiently cross presented and the presence of additional molecular chaperone proteins in the autophagosome enriched composition may serve to preserve these antigens, furthering their efficiency for cross presentation.

Additionally, autophagosome enriched vaccines may be effective stimulators of targeted immune response as they present a variety of tumor associated antigens. These antigens may also be uniquely preserved in the composition as the autophagosomes also contain protein chaperone molecules such as HSP-90, HSP-70, and calreticulin which may act to protect the integrity of the antigens. Furthermore, the autophagosomes contain damage-associated molecular patterns (DAMPs). These DAMPs are present in necrotic cells and elsewhere and may act as a natural adjuvant contained within the vaccine. DAMPs present in AAECs may include HMGB1, S100 proteins, DNA, and RNA. Autophagosome enriched compositions may contain toll-like receptor (TLR) agonists. These TLR agonists stimulate the innate immune response, which may be beneficial to patients who have reduced immune function secondary to age, cancer therapy, or effects of progressive tumor growth.

Moreover, the AAECs, and autophagosome enriched compositions in general, are appropriate candidates for co-administration with molecules that serve as adjuvants or otherwise. In one example, the vaccine was administered to DCs in conjunction with IFN-γ and TLR agonist, molecules known to induce immune response. This combination was shown to induce a robust anti-tumor response to 3LL lung carcinoma and B16F10 melanoma. Non-specific adjuvants, such as alum, CpG, GM-CSF, Flt3L or combinations thereof may be administered in conjunction with the autophagosome enriched compositions. Specific adjuvants or therapeutics that are targeted towards specific cell or tissue types may be administered in conjunction with an autophagosome enriched vaccine in order to locate the immune response within said cell or tissue populations.

In addition to co-administration with an adjuvant or related compound, the vaccine may be formulated with additional compounds including those with independent therapeutic utility or that may preserve chemical components within the AAECs.

A course of treatment may include multiple rounds of vaccine administration. Each round of vaccine administration may utilize various adjuvants or combinations of adjuvants. This course of action may be determined in advance of the initial vaccine administration or may be informed by the patient response to the vaccine and accompanying adjuvants as assessed by molecular, cellular or systemic assays, imaging procedures or other such tests to monitor the patient response. In one example described below, the AAECs may be used to stimulate the production of BDCA3+ (blood dendritic cell (DC) antigen-3+) monocytes, which stimulate an inflammatory response. These monocytes may be isolated and administered as an adjuvant in conjunction with subsequent rounds of vaccination.

In order to accumulate DRiPs and SLiPs into AAECs, Velcade or similar proteasome inhibitors had been used previously, thereby preventing the DRiPs and SLiPs from being degraded by the proteasome. Proteasome inhibition also increases autophagy, however, the inventors have determined that this may not be the most efficient way to increase autophagy.

The autophagosome enriched composition of this disclosure comprises multiple TLR agonists and multiple tumor antigens. Proteasome inhibition may limit the composition with regards to antigens necessary to stimulate a response against infectious disease and may limit the composition with regards to proteins necessary to stimulate membrane-protein transfer. Therefore, the autophagosome-enriched composition may be produced through contact with agents that are known in the art to enrich autophagosomes without proteasome inhibition, such as $NH_4CL$, chloroquine, rapamycin, or other autophagy stimulating agents. Autophagy may also be induced in cells or tissues through means of starvation.

Antigen cross-presentation by professional antigen-presenting cells (pAPC) is the first step for the development of adaptive immune responses to antigens that are not synthesized by pAPC, such as tumor-associated antigens or viral antigens where direct presentation by pAPC is subverted by viral escape mechanisms. In these examples, the antigens available for cross-presentation are derived from dead or dying cells. The inventors herein have identified a novel autophagy-assisted antigen cross-presentation pathway (AAAXP) for these antigens. This pathway may regulate the efficiency of antigen cross-presentation by specific recognition of autophagosomes via the CLEC9A receptor on a subset of dendritic cells that are highly efficient at cross-presenting dead cell-associated antigens. The inventors have recognized that vaccination with tumor-derived autophagosomes conferred heterologous protection from tumor challenge and high therapeutic efficacy in multiple models of established murine tumors.

AAECs may be cross-presented exclusively by mouse $CLEC9A^+PDCA-1^{dim}$ dendritic cells (referred to here as xDC), but not $CLEC9A^-CD8\alpha^+$ cDC or $CLEC9A^-PDCA-1^{hi}$ pDC. Gene array analysis revealed that xDC are more closely related to pDC than $CD8\alpha^-$ cDC. Additionally, functional xDC may be found in bone marrow (BM) in chimeric mice either after depletion of pDC or after reconstitution with Batf3 deficient BM. However, xDC are lost in chimeric mice that were reconstituted with IRF8 deficient BM. Additionally, $CLEC9A^+CD11c^-$ xDC precursors (pre-xDC) may be found in BM and spleen of mice and may differentiate into functional cross-presenting dendritic cells (xDC) upon phagocytosis of AAECs. Furthermore, the human equivalent of mouse xDC and pre-xDC as characterized by CLEC9A and BDCA expression may be present in human PBMC and G-CSF mobilized blood.

Example 1

Figure 1:
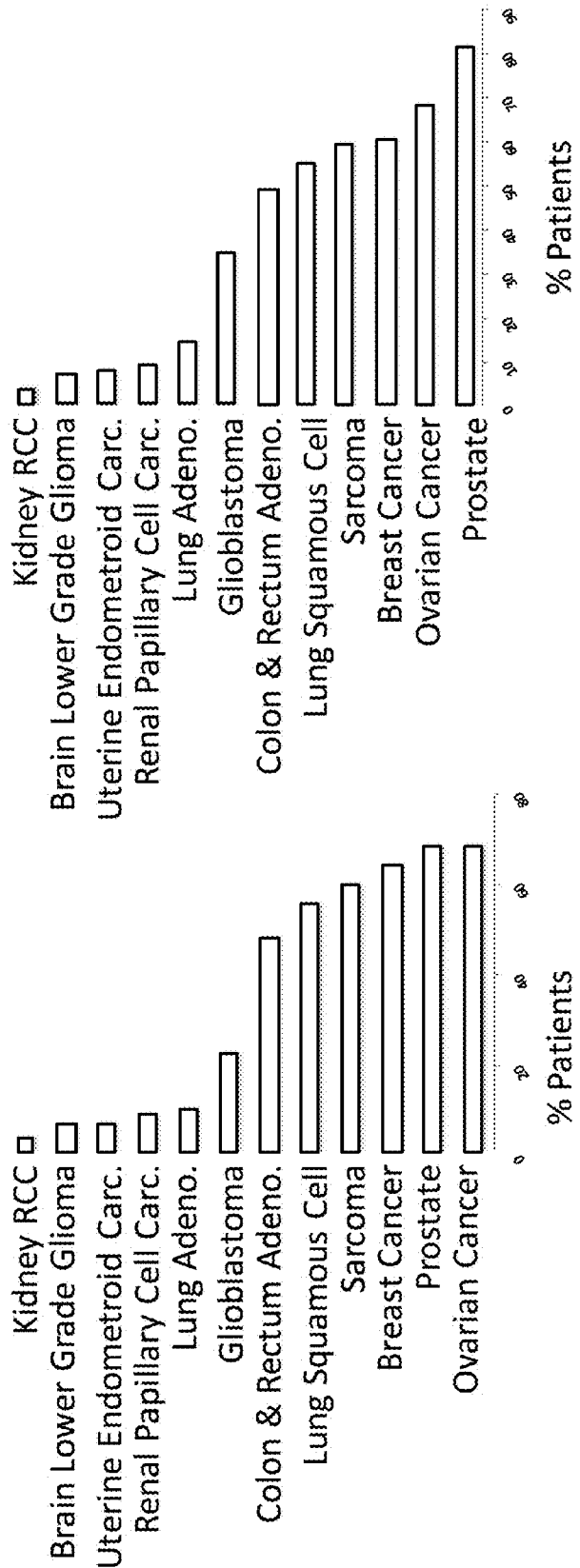
FIG. 1 is a graph displaying the percentage of patients with various types of cancer that share an upregulation of the top 500 most upregulated genes in UbLT3 and UbLT6 NSCLC cell lines.

An Allogeneic Autophagosome Enriched Composition and a Method for Producing the Composition FIG. 1 depicts the percentage of patients with various forms of cancer that have upregulation in those genes that are among the 500 most upregulated genes in the UbLT3 or UbLT6 cell lines. The data are from the following cancer types with number of patients in parentheses: Ovarian (232 patients), Prostate (85 patients). Breast (451 patients), Sarcoma (149 patients). Lung Squamous (178 patients), Colon (193 patients), Glioblastoma (122 patients), Adenocarcinoma (112 patients), Renal Papillary (75 patients), Uterine (232 patients), Glioma (144 patients), and Kidney RCC (389 patients). As shown in FIG. 1, microarray analysis of NSCLC cell lines UbLT3 & UbLT6 (each compared to normal lung RNA) after treatment with Velcade & $NH_4Cl$ shows that many genes up-regulated in these cell lines are also up-regulated in other cancers in the Cancer Genome Atlas (TCGA) datasets. The top 500 genes most significantly upregulated (SAM Excel) were compared to microarray data in TCGA (z score >3). Data show that UbLT3 and UbLT6 treated tumor cells share at least one gene in common with many patients' tumors of varying etiology. Notably, many patients' cancers have hundreds of upregulated genes in common with UbLT3 and UbLT6 of the 500 hundred genes checked, including patients with ovarian cancer, prostate cancer, breast cancer, sarcoma, lung squamous cell sarcoma, and colon & rectum adenocarcinoma. Although microarray data was not available for HNSCC, RNASeq datasets for 291 HNSCC patients show an average of 25 common genes expressed per sample compared to UbLT3 and 29 for UbLT6 out of 300 genes analyzed (data not shown).

Previously, the inventors herein disclosed methods for producing and isolating a variant of AAECs known as DRibbles (US 2009/0220530). For the purposes of this disclosure, the terms "Allogeneic Autophagosome Enriched Compositions" or "AAECs" and "DRibbles" may be used interchangeably, but it should be understood that AAECs refer to a specific subset of DRibbles). The method includes contacting the target cell with a sufficient amount of proteasome inhibitor under conditions sufficient for producing AAECs, such as conditions that substantially inhibit protein degradation in the cell. In some examples, the method further includes contacting the target cell with a sufficient amount of an autophagy inducer before, during or after contacting with the proteasome inhibitor. The cell may also be contacted with one or more agents that decrease glycosylation of proteins. In one example, the cell is contacted with sufficient amounts of a proteasome inhibitor (such as 20 nM Velcade), an autophagy inducer (such as rapamycin or HBSS) and $NH_4Cl$ under conditions sufficient to stimulate production of AAECs by the cell. In one example, the AAECs produced under said conditions are harvested by separating said AAECs from the cell. In one exemplary method, a cell may be contacted with a sufficient amount of a composition that may include a proteasome inhibitor under conditions sufficient to substantially inhibit protein degradation in a cell, for example an incubation of 6-24 hours. The cells may then be incubated under conditions sufficient to induce autophagy in the cell, for example an incubation of 6-24 hours with an autophagy inducer. In some embodiments, the cell lines with a high basal autophagy rate may be incubated under conditions sufficient to leverage the cells' ongoing autophagy. The resulting cells and AAECs may then be centrifuged under conditions such that the cells are pelleted while the AAECs remain in solution. The supernatant containing the AAECs may then be removed and may then be centrifuged under conditions sufficient to pellet the AAECs. In other embodiments, the cells may be sonicated to stimulate release of autophagosomes. The resulting milieu is then centrifuged to remove cells and high-density cell debris, such that the cleared supernatant retains the AAECs in solution. The AAEC containing solution may then be centrifuged under conditions to pellet the AAECs. The pelleted AAECs may then be washed and suspended in a suitable buffer for downstream applications.

Figure 2A:
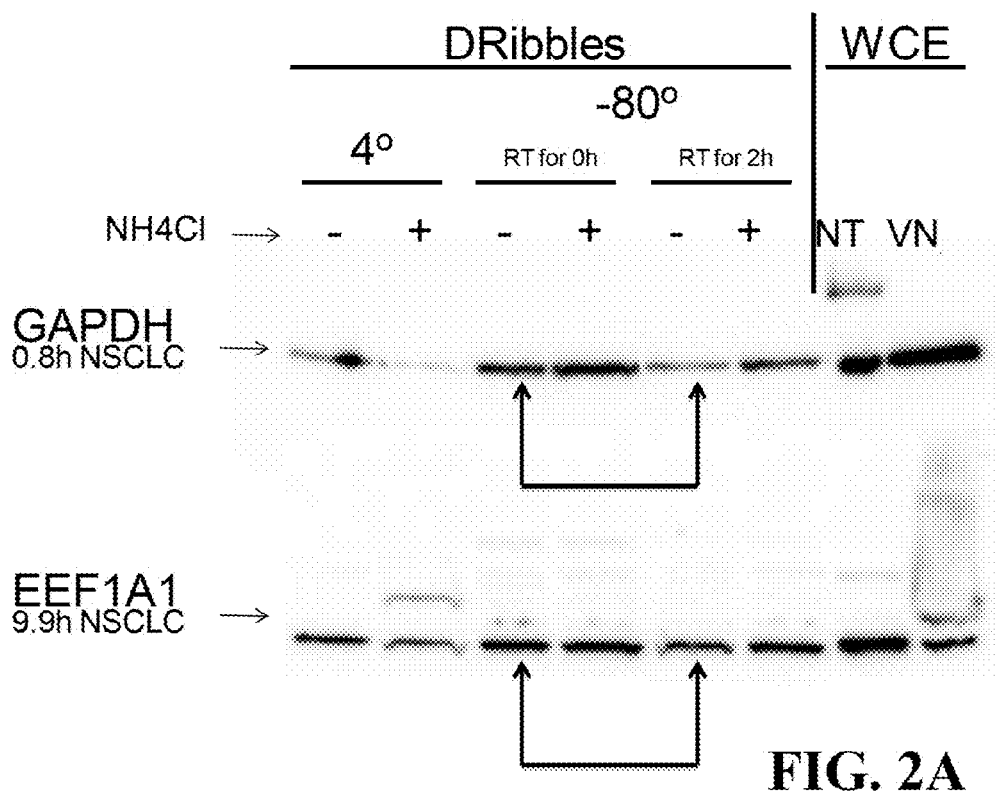
FIG. 2A is a digital image showing an SDS-page gel indicating the presence of $NH_4Cl$ protects against degradation of antigens GAPDH and EEF1A1.
Figure 2B:
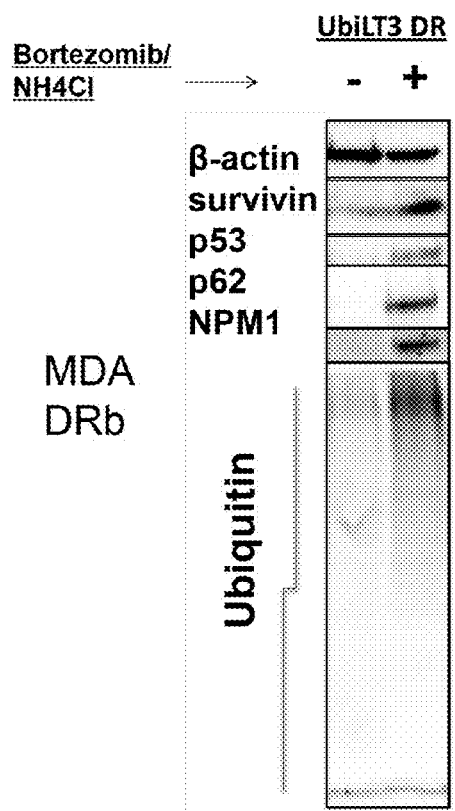
FIG. 2B is a digital image showing an SDS-page gel showing that velcade treatment increases the ratio of ubiquitinated proteins and short-lived antigens in AAECs generated from the treated cells.

FIG. 2A is a digital image showing an SDS-page gel indicating the presence of $NH_4CL$ protects against degradation of proteins GAPDH and EEF1A1. In this way, peptide antigens may be protected from degradation and packaged into the AAEC. As shown in FIG. 2B, treatment of cells with Velcade and $NH_4Cl$ alters the protein composition of the resulting AAECs, when compared to AAECs produced without treatment. The treatment with Velcade and $NH_4Cl$ increased the relative content of ubiquinated proteins and short-lived antigens. For example, AAECs generated by treated cells have an increased ratio of ubiquitinated protein to Beta-actin. NPM1, p62, p53, and surviving are all present in higher ratios to Beta-actin than for AAECs generated from untreated cells.

Figures 3C, 3D:
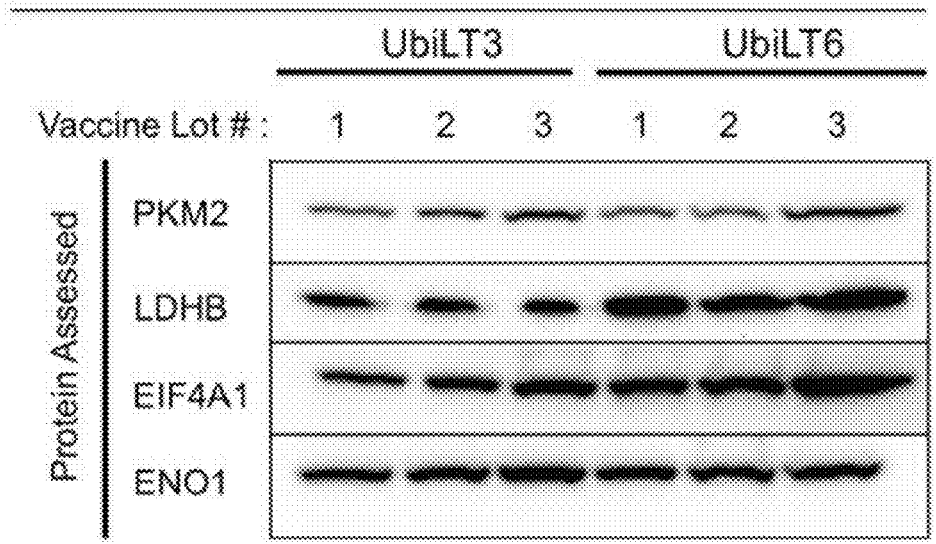
FIG. 3C is an additional chart which tabulates the presence of NCI prioritized cancer antigens in AAECs.
FIG. 3D shows additional antigens and the consistency of detection in multiple lots over time.

The AAECs represent a promising therapeutic for cancer as they may contain at least 6 National Cancer Institute (NCI) prioritized cancer antigens. FIG. 3A shows gene profiling of UbLT3 & UbLT6 cells treated with Velcade & $NH_4Cl$ along with normal lung RNA that was done on Affymetrix Human Gene 1.0 ST arrays. Expression was compared to the NCI top cancer antigen prioritization list. Gene profiling was done on 3 independent RNA samples for each condition. Standard Deviation of expression for all the genes shown is less that 5% FIG. 3B shows protein expression of 6 antigens (WT1, p53, Survivin, EphA2, Cyclin B1, & XAGE1), with gene expression in UbLT3 or UbLT6 cells, was confirmed in DRibbles by western blot. FIG. 3C shows additional confirmation of the presence of NCI prioritized antigens in UbLT3 and UbLT6 derived AAECs. Antigens include WT1, EGFRvIII, HER-2/neu, p53, Survivin, EphA2, Cyclin B1, XAGE 1, and PDGFR-β. FIG. 3D shows the presence of four NSCLC targets in UbLT3 and UbLT6 derived AAECs as demonstrated by western blot. Target proteins include PKM2, LDHB, EIF4A1, and ENO1. A summary table indicating antigens comprising in the UbLT3 and UbLT6 AAECs is shown in FIG. 3E.

Figures 4A, 4B:
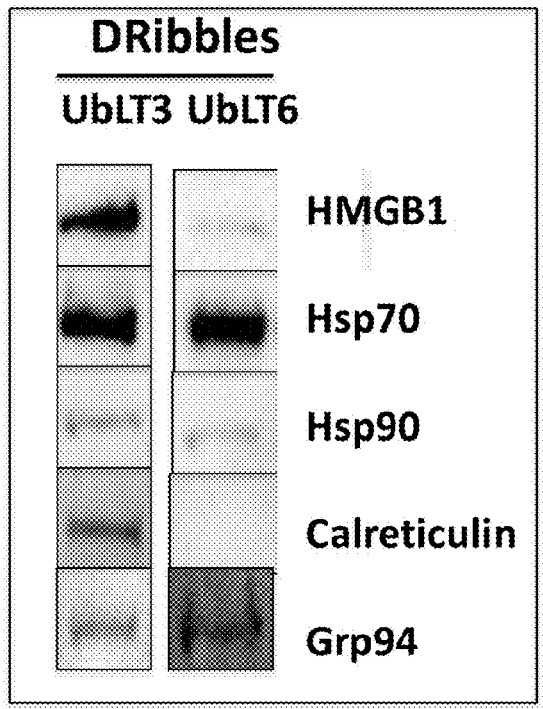
FIG. 4A is a chart tabulating the presence of DAMPs in AAECs.
FIG. 4B is a digital image showing an SDS-page gel indicating the presence of various DAMPS in AAECs derived from two different cell lines.

Additionally, DAMPs may be highly expressed in treated UbLT3 and UbLT6 cells as indicated by microarray data and in the AAECs as shown by SDS PAGE gel electrophoresis. DAMPs are capable of initiating and perpetuating immune responses via the non-infectious inflammatory response, essentially sending a "Danger" signal to the immune system. FIG. 4 A-B shows this data. FIG. 4A shows gene profiling of UbLT3 & UbLT6 cells treated with Velcade & $NH_4Cl$ and normal lung RNA that was done on Affymetrix Human Gene 1.0 ST arrays. Expression was compared to the NCI top cancer antigen prioritization list (Cheever, et al. Clin Cancer Res. 2009: 5323-5337). Gene profiling was done on 3 independent RNA samples for each condition. Standard Deviation of expression for all the genes shown is less than 5%. FIG. 10B shows protein expression of 6 antigens (WT1, p53, Survivin, EphA2, Cyclin B1, & XAGE1), with gene expression in UbLT3 & UbLT6 cells confirmed in AAECs by western blot.

Figure 5A:
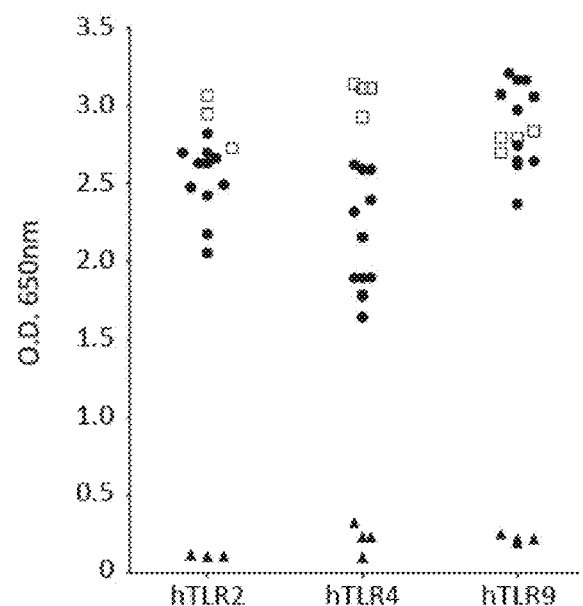
FIG. 5A is a graph displaying data indicating AAECs contain high levels of TLR ligands.
Figure 5B:
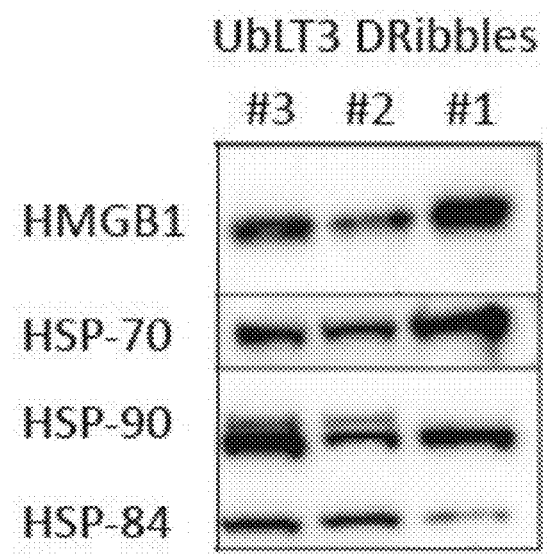
FIG. 5B is a digital image displaying data indicating AAECs contain DAMPs.

When processed using the methods described herein (e.g. treatment with proteasome inhibitors and $NH_4Cl$) the UbLT3 AAECs express high levels of TLR ligands and DAMPs. The toll-like receptors comprise a class of proteins expressed on the surface of cells, such as macrophages and dendritic cells, and are capable of recognizing and binding molecules associated with cell stress and/or pathogens. Upon binding to a TLR-agonist, the TLR becomes activated and sets off a signaling cascade resulting in the production of inflammatory cytokines and/or type 1 interferons. FIGS. 5A and 5B show data on expression of TLR ligands in AAECs. In FIG. 5A the presence and potency of TLR-2, -4 or -9 agonists within the UbLT3 AAEC was assessed using HEK-293 cells transduced to express a single human TLR (Invitrogen). Potency was compared to positive and negative (no ligand) controls. FIG. 5B shows a western blot showing protein expression of DAMPs in 3 different batches of UbLT3 AAEC.

Figure 6:
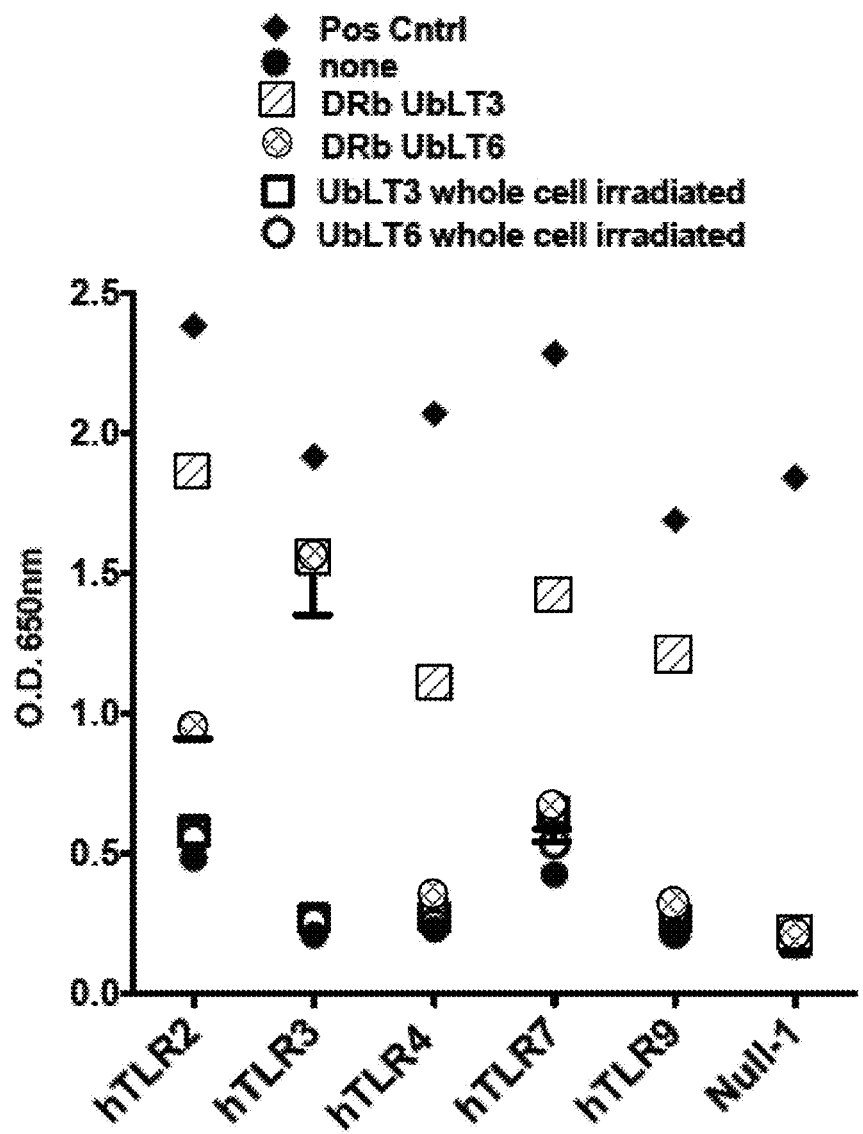
FIG. 6 is a graph indicating the presence of TLR ligands in AAECs.

Additionally, the AAECs may contain multiple TLR ligands. These TLR ligands mimic microbial antigens and stimulate the innate immune response, which is beneficial when administering the AAEC to patients. FIG. 6 indicates the presence of various TLR ligands by their activity in HEK-Blue cells by visual-spectography. HEK-Blue cells transfected with a single human TLR were used to measure TLR agonists in AAECs (Invitrogen). UbLT3 and UbLT6 AAECs contain agonists for TLR 2, 3, 4, 7 and 9. AAECs were added at 50 ug/ml. Whole cell irradiated tumors were added at $10^5$/ml. Positive controls are: TLR2 (LTA) @500 ng/ml, TLR3 (poly (I:C), LMW)@10 μg/ml, TLR4 (LPS) @500 pg/ml, TLR7 (CL097) @50 μg/ml, TLR9 (ODN 2006) @ 10 μg/ml, NULL1 (TNFalpha@1000 ng/ml).

The data described herein and with regards to FIGS. 1-6 may enable one or more compositions, and one or more methods for screening cells that produce these compositions. A composition, comprising: an enriched population of autophagosomes derived from a non-small cell lung carcinoma cell line, and wherein the enriched population of autophagosomes includes: one or more toll-like receptor agonists; one or more tumor antigens; and one or more damage-associated molecular pattern molecules. The one or more toll-like receptor agonists may include agonists for toll-like receptor 2, toll-like receptor 3, toll-like receptor 4, toll-like receptor 7, and/or toll-like receptor 9, or a combination thereof. The one or more tumor antigens may include WT1, p53, Survivin, EphA2, Cyclin B1, and/or XAGE1 or a combination thereof. The one or more damage-associated molecular pattern molecules may include calreticulin, HMGB1, HSP70, HSP90, and/or Grp94 or a combination thereof. In some examples, the enriched population of autophagosomes may be derived from the UbLT3 cell line. In some examples, the enriched population of autophagosomes may be derived from the UbLT6 cell line. The composition may further comprise a molecule configured to augment the immune response against the antigens comprising the enriched population of autophagosomes. The molecule may be polyinosinic:polycytidylic acid. The composition may further comprise a non-specific adjuvant.

In another example, a method for screening cells that produce allogeneic autophagosome enriched compositions able to induce expression of a selective marker on a subpopulation of peripheral blood mononuclear cells, comprising: contacting a cell with a proteasome inhibitor; contacting the cell with a lysosome inhibitor; harvesting the resulting autophagosomes; determining a molecular signature of the resulting autophagosomes; and selecting cells that divert one or more Toll-like receptor agonist and/or one or more molecular chaperones to the autophagosomes. The selective marker may be BDCA3 and the subpopulation of peripheral blood mononuclear cells may include dendritic cells. The selective marker may be CD80 and the subpopulation of peripheral blood mononuclear cells may include monocytes.

Example 2

Induction of Pro-Inflammatory BDCA3 Expressing Monocytes in Human PBMC

A second example describes a method that may induce an increase in BDCA3 expressing monocytes in human PBMC and single cell suspensions from lymph nodes (LN) using the AAECs.

BDCA3 expressing dendritic cells (DCs), upon stimulation by toll-like receptor 3 (TLR3) produce interleukin-12 (IL-12) and interferon-β, cytokines known to enhance T helper type 1 (TH1) and cytotoxic T lymphocyte (CTL) response. BDCA3+ DCs are also important for cross presentation to CD8+ cells. Because of these activities, BDCA3+ DCs may be important for stimulating an anti-tumor immune response.

As described above, the AAECs may be produced by tumor cells upon combined inhibition of proteasomal degradation and lysosome-mediated proteolysis and may contain a variety of tumor antigens as well as DAMPs and to TLR ligands. AAECs are efficiently taken up by murine CLEC9A+ cross-presenting dendritic cells and may be capable of eliciting therapeutic immunity to established murine tumors. Here the inventors describe the interactions and effects AAECs may have on human myeloid cells using PBMC and single cell suspensions from lymph nodes.

FIG. 7 shows an example where AAECs were efficiently taken up by blood CD14+BDCA3− monocytes. Interaction with AAECs resulted in a dose-dependent induction of the blood DC marker BDCA3 on monocytes. BDCA3 upregulation on monocytes could be partially blocked by TLR9 blockade using blocking oligodeoxyribonucleotides (ODN).

In clinical samples, melanoma patients vaccinated with a combination of GM-CSF and CpG displayed increased levels of CD14+BDCA3+ cells in their tumor-draining LN. Similar to AAECs, in vitro stimulation with GM-CSF and CpG or CpG alone led to BDCA3 induction both on monocytes and CD11c+CD14− DC. In addition to blood monocytes, AAECs may also increase BDCA3 expression on CD14+CD11c+ cells present in LN single cell suspensions of melanoma patients. In these samples, BDCA3 induction correlated with enhanced levels of secreted IL-8 in the supernatant (r=0.76, p<0.01). Indeed, sorted AAEC-induced CD14+BDCA3+ cells from PBMC produced higher levels of IL-8 compared to CD14+BDCA3− cells from the same culture or sorted vehicle-treated BDCA3− monocytes. While IL10-induced CD14+BDCA3+ tissue DC have been described to be tolerogenic and suppress T cell responses, the inventors found AAEC-induced CD14+BDCA3+ monocytes may stimulate CD4 and CD8 T cell proliferation in a concentration-dependent manner in the presence of a suboptimal dose of anti-CD3 antibody. CD4 and CD8 T cells in these co-cultures may produce high levels of the Th1 cytokines, IFN γ and TNFα, the latter correlating with proliferation (r=0.97, p<0.001), suggestive of a possible pro-inflammatory role for AAEC-activated monocytes.

Figure 7A:
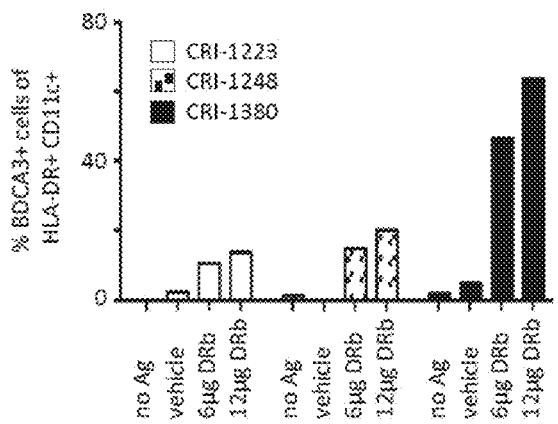
FIG. 7A is a graph displaying data indicating a dose dependent increase in percentage of BDCA3+ cells after treatment with AAECs.
Figure 7B:
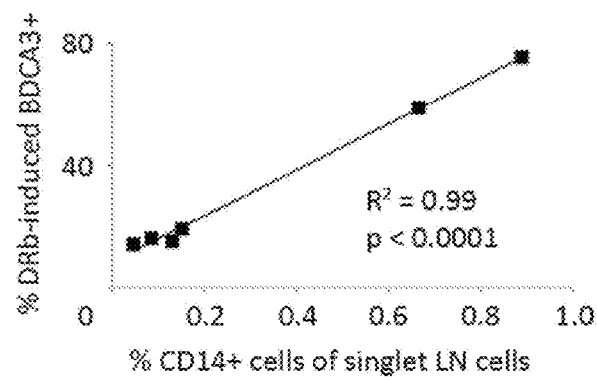
FIG. 7B is a graph displaying data indicating induction of CD14+ cells and BDCA3+ cells are correlated.
Figure 7C:
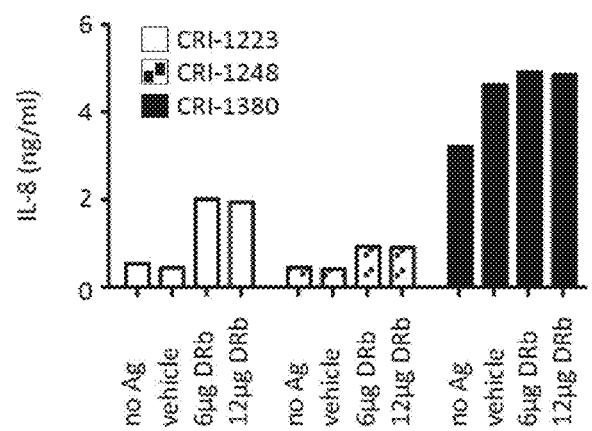
FIG. 7C is a graph displaying data indicating a dose dependent increase in IL-8 concentration after treatment with AAECs.

Induction of BDCA3 expression on HLA-DR+ CD11c+ cells present in LNs, and increased IL-8 secretion, correlate with frequencies of CD14+ cells present in the cultures. CD14+ cells are monocytes that can differentiate into a variety of different cell types. Their increased frequency correlated to induction of BDCA3 expression is indicative of the pro-inflammatory response of BDCA3 expression. FIG. 7A-C depict data indicating a dose dependent induction of BDCA3 specific to the AAEC and this induction is correlated (R2=0.99, p<0.001) to increasing CD14+ cells. This correlation suggests that the AAEC may be involved in upregulation of CD14+ cells which may be beneficial to induction of an immune response. Cryopreserved melanoma LN single cell suspensions were thawed and co-cultured with nothing (no Ag), heta starch (vehicle), 6 µg or 12 µg UbLT3 AAEC (DRb) in X-vivo 15 medium for 20 hours (1 million cells/ml in a 48-well plate). FIGS. 7A and 7B show harvested cells that were characterized by 12-color flow cytometry, looking at CD11c, CD14, CD1a, HLA-DR, CD11b, CD80, CD86, CD103, BDCA3/CD141 and CD83. Dead cells were excluded by means of a live/dead stain and gates were set based on Fluorescence Minus One (FMO) controls. FIG. 7B shows the Pearson correlation between AAEC-induced BDCA3 expression on CD11c+DR+ cells and frequencies of CD14+ cells. FIG. 7C shows induction of IL-8 in the same experimental assay supernatants that were removed prior to harvest. Secreted cytokines were assessed by cytokine bead array.

Figure 8A:
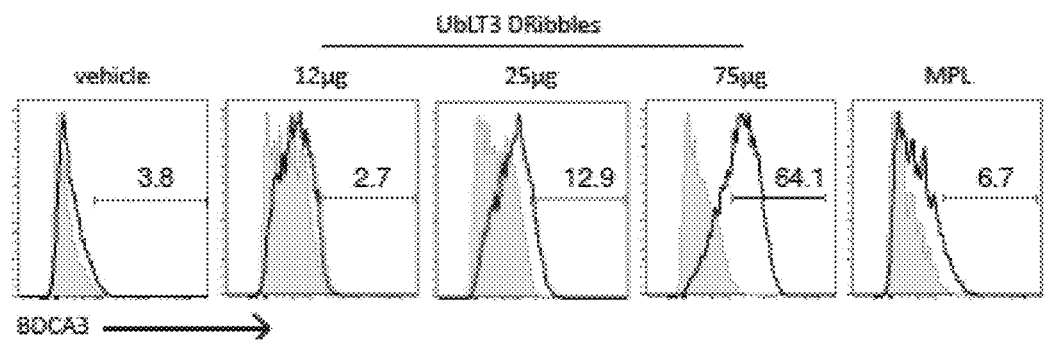
FIG. 8A is a cytometry plot displaying data indicating a dose dependent increase in percentage of BDCA3+ cells in human CD14+ cells after treatment with a UbLT3 derived AAEC.
Figure 8B:
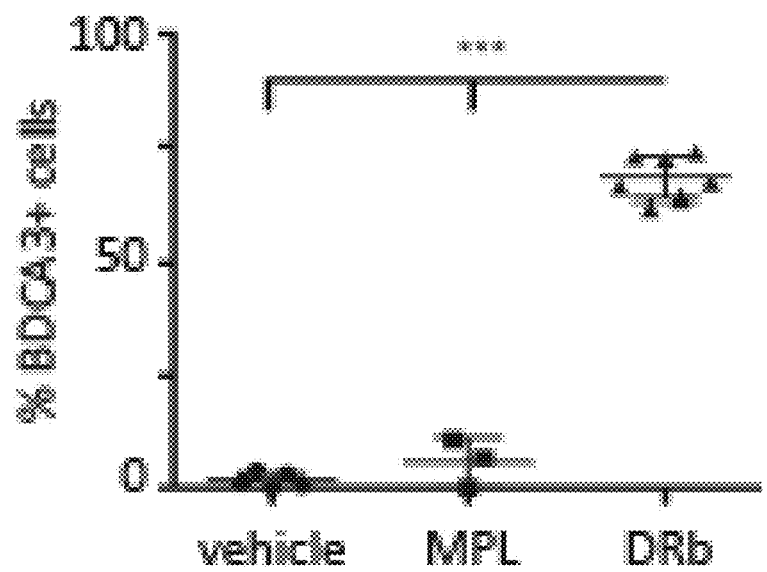
FIG. 8B is a graph displaying data indicating AAECs are a better inducer of BDCA3+ cells than vehicle or TLR4 agonist MPL.

AAECs may induce expression of BDCA3 on CD14+ human monocytes. FIGS. 8A-B depict experimental data indicating expression of BDCA3 is increased on CD14+ human monocytes. For the experiments, healthy donor PBMC (1 million/ml) were co-cultured with heta starch (vehicle), and treated with increasing concentrations of UbLT3 AAEC or the TLR4 agonist MPL (500 ng/ml). Cells were then phenotyped by flow cytometry after 20 h. FIG. 8A shows histogram plots from one representative donor. The shaded graphs represent specimen-specific (fluorescence minus one) FMO controls. The open graphs show BDCA3–FITC expression on HLA-DR+ CD11c+ CD14+ monocytes. FIG. 8B depicts a graph representing 3 separate experiments with 2 healthy donors, using 75 µg AAEC (DRb). *** p<0.0001 One-way Anova with Tukey's multiple comparison test (Prism).

TLR-9 inhibition reduces AAEC-mediated induction of BDCA3 expression on CD14+ monocytes and reduces IL-8 secretion in AAEC-touched PBMC cultures. TLR-9 may be blocked by specific ODNs, blockade of this receptor inhibits activation of intracellular pathways within TLR-9 expressing cells that, overall, lead to activation of an immune response. Experiments shown in FIGS. 9A-D were performed in human PBMC (2×105 in 200 µl in 96-well plate) that were cultured with vehicle, UbLT3 DRibbles (75 µg/ml) after 20 min incubation at 37° C. with or without TRL2, TRL4 or TRL9 antagonists or controls. FIG. 9A shows histogram plots showing BDCA3 expression (open) and FMO controls (shaded), using the highest concentration of anti-TLRs (7.5 µg/ml for T LR2/4, 13.8 µM for TLR9). FIG. 9B shows % BDCA3+ CD14+ cells with titration of anti-TLR9 and control ODN for 2 donors. FIG. 9C shows IL-8 secretion in the PBMC AAEC-touched cultures +/−TLR antagonists as determined by CBA. FIG. 9D shows AAEC uptake by PBMC incubated in various TLR antagonists. UbLT3 AAECs were loaded with 0.5 µM far red lipid dye (3 min RT) then washed and co-cultured with 2×105 PBMC pre-incubated with TLR antagonists for 2 hours. PBMC cultured with UbLT3 AAEC at 4° C. were used as control for active uptake (n=1, in duplicate).

Figure 9E:
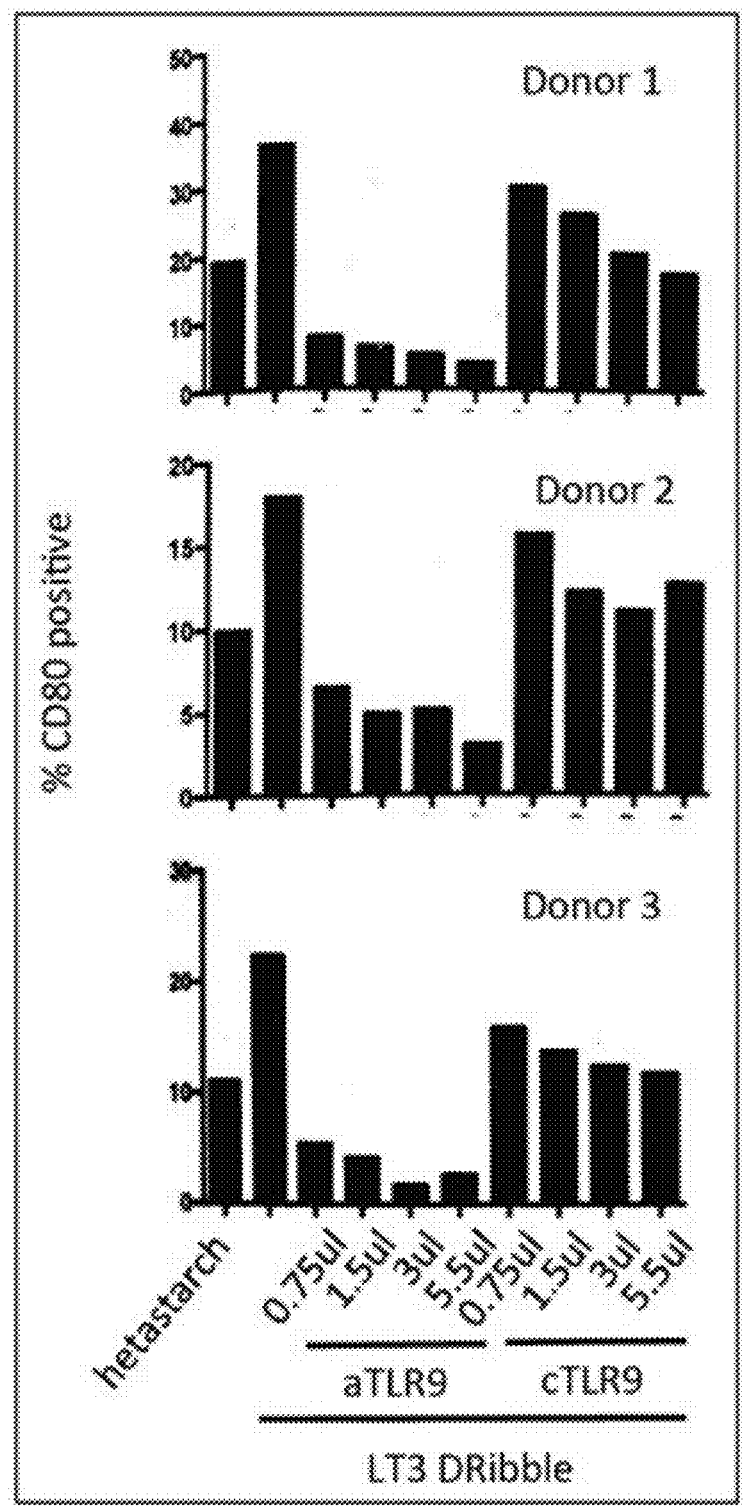
FIG. 9E is a graph displaying data indicating that the AAECs that upregulate expression of CD80 on monocytes do so, at least in part, through a TLR9 pathway.

FIG. 9E shows that UbLT3 derived AAECs added to PBMC from three donors increase the percent of monocytes that express CD80, a costimulatory molecule associated with maturation of these antigen presenting cells. This effect can be inhibited by blocking signaling through TLR9, but not by adding a mock-inhibitor of TLR9.

Figure 10:
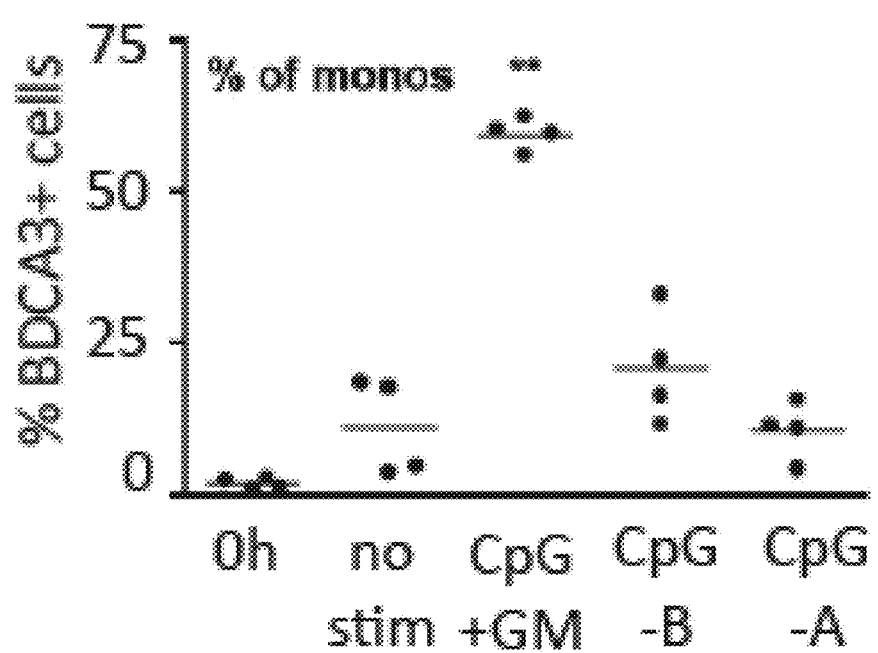
FIG. 10 is a graph indicating the percentage of BDCA3+ cell induction in response to various treatments.

FIG. 10 shows the induction of BDCA3+ cells in response to various treatments to CD14+ monocytes of PBMC from four healthy donors. Experiments were performed in PBMC (5 million/ml in a 48-well plate in IMDM+10% FBS) that were cultured for 48 h without stimulation (no stim), 5 µg/ml CpG-A (ODN-2216), 5 µg/ml CpG-B (ODN-7909) or CpG-+ 1000 IU/ml GM-CSF (CpG+GM). BDCA3+ expression on CD14+ monocytes was assessed by 4-color flow cytometry (VUmc).

Figure 11A:
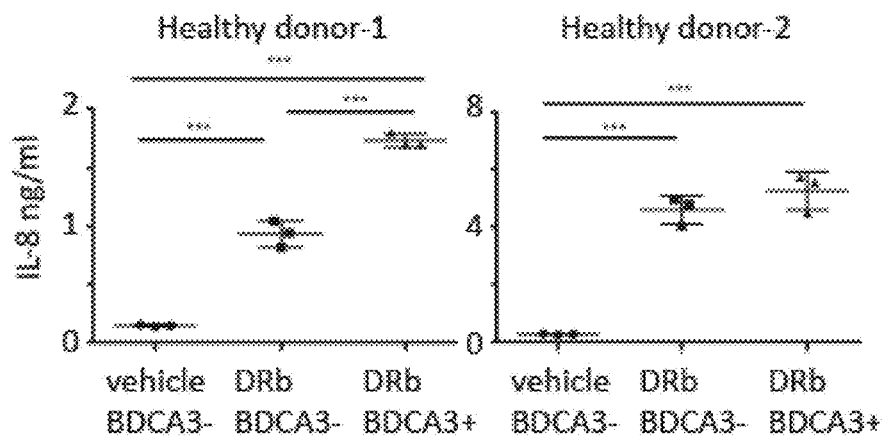
FIG. 11A is a graph indicating the concentration of IL-8 in cells from two donor patients in response to different treatments.
Figure 11B:
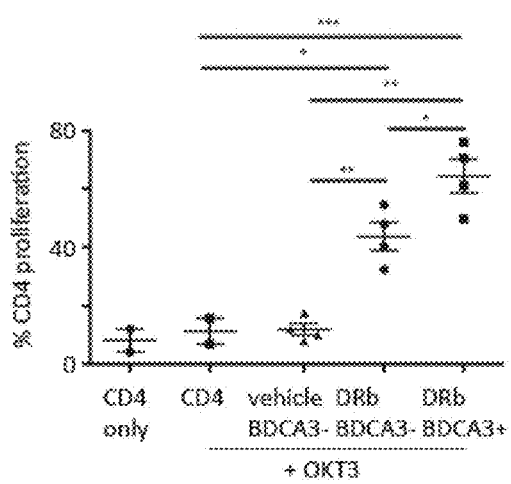
FIG. 11B is a graph indicating the proliferation of CD4+ cells in the presence of AAEC touched CD14+ cells.
Figure 11C:
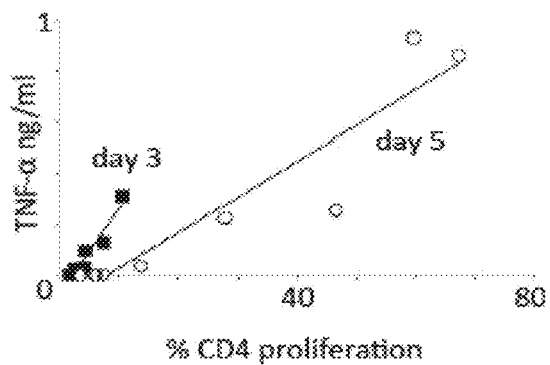
FIG. 11C is a graph indicating the secretion of TNF-α as a function of CD4+ cell proliferation.

AAEC-contacted monocytes, both BDCA3− and BDCA3+, produce high levels of IL-8 and stimulate T cell proliferation in combination with suboptimal anti-CD3 stimulation. Stimulation of T cell proliferation is used as an indication of the induction of an immune response. Increased proliferation of CD4 in the presence of an AAEC is beneficial as the composition may be administered to patients in order to stimulate an immune response toward a targeted cancer antigen, infection, or other illness in which a targeted immune response is beneficial. FIGS. 11A-B depicts data indicative of the upregulation of IL-8 and T-cell proliferation. For these experiments PBMC of two healthy donors were co-cultured with vehicle or 75 µg/ml UbLT3 AAEC for 20 h. CD4+ CD25− and CD8+ T cells and CD14+ (BDCA3−) monocytes were sorted from the vehicle treated samples. CD14+ BDCA3− and CD14+BDCA3+ cells were sorted from the AAEC-treated samples. Sorted CD14+ cells from donor-1 were co-cultured with sorted T cells from donor-2 and vice versa. FIG. 11A depicts IL-8 concentration from 5000 sorted CD14+ cells that were cultured overnight in RPMI+10% FBS. The supernatants were harvested after 20 h (triplicates per sample) (2 experiments with similar results). FIG. 11B shows proliferation of CD4 T cells that were stimulated with 2 µg plate-bound OKT3 (anti-CD3) in the presence of sorted vehicle or AAEC-treated CD14+. In FIG. 11C TNF-α concentration is correlated with the proliferation of CD4 at both day 3 and day 5.

UbLT3 AAECs may be found to induce BDCA3 expression on CD11c+ HLA-DR+ cells in human melanoma LN samples. The level of induction correlated with the presence of CD14+ cells in these samples. Similar to LN samples, AAECs induced BDCA3 expression on healthy donor monocytes. MPL, a TLR4 agonist did not induce BDCA3 expression on human monocytes, suggesting a TRL4-independent mechanism. UbiLT3 AAECs may be found to express high levels of ligands stimulating various TLRs. Inhibition of TLR2, TLR4 or TLR9 activation showed a contribution of TLR9 in AAEC-induced BDCA3 induction (observed in 2 donors). Interestingly, melanoma patients treated with intradermal injection of CpG or CpG+GM-CSF displayed enhanced frequencies of BDCA3+ DC subsets in their sentinel LNs (Sluijter et al. in preparation). In vitro stimulation of PBMC with CpG or CpG+GM-CSF induced BDCA3 on CD14+ monocytes, confirming a link between TLR9 stimulation and BDCA3 expression on monocytes. In addition to BDCA3 induction, AAECs may induce production of IL-8 in melanoma LN and healthy donor PBMC cultures. In 2/2 PBMC donors, TLR9 inhibition reduced IL-8 production, whereas TLR4 inhibition reduced IL-8 levels in 1/2 donors (1 exp). Sorted AAEC-induced BDCA3+ cells produced significantly higher levels of IL-8 than control monocytes (2 exps with 2 donors each). In contrast to non-treated monocytes, BDCA3+ and BDCA3-monocytes sorted from AAEC-treated PBMC may stimulate CD4 T cell proliferation (+OKT3) and IFN-γ production (not shown). AAEC-induced BDCA3+ monocytes in addition, stimulated CD8 T cell proliferation (not shown) and TNF-α production. These data suggest that AAECs may induce pro-inflammatory changes in human monocytes.

Figure 12A:
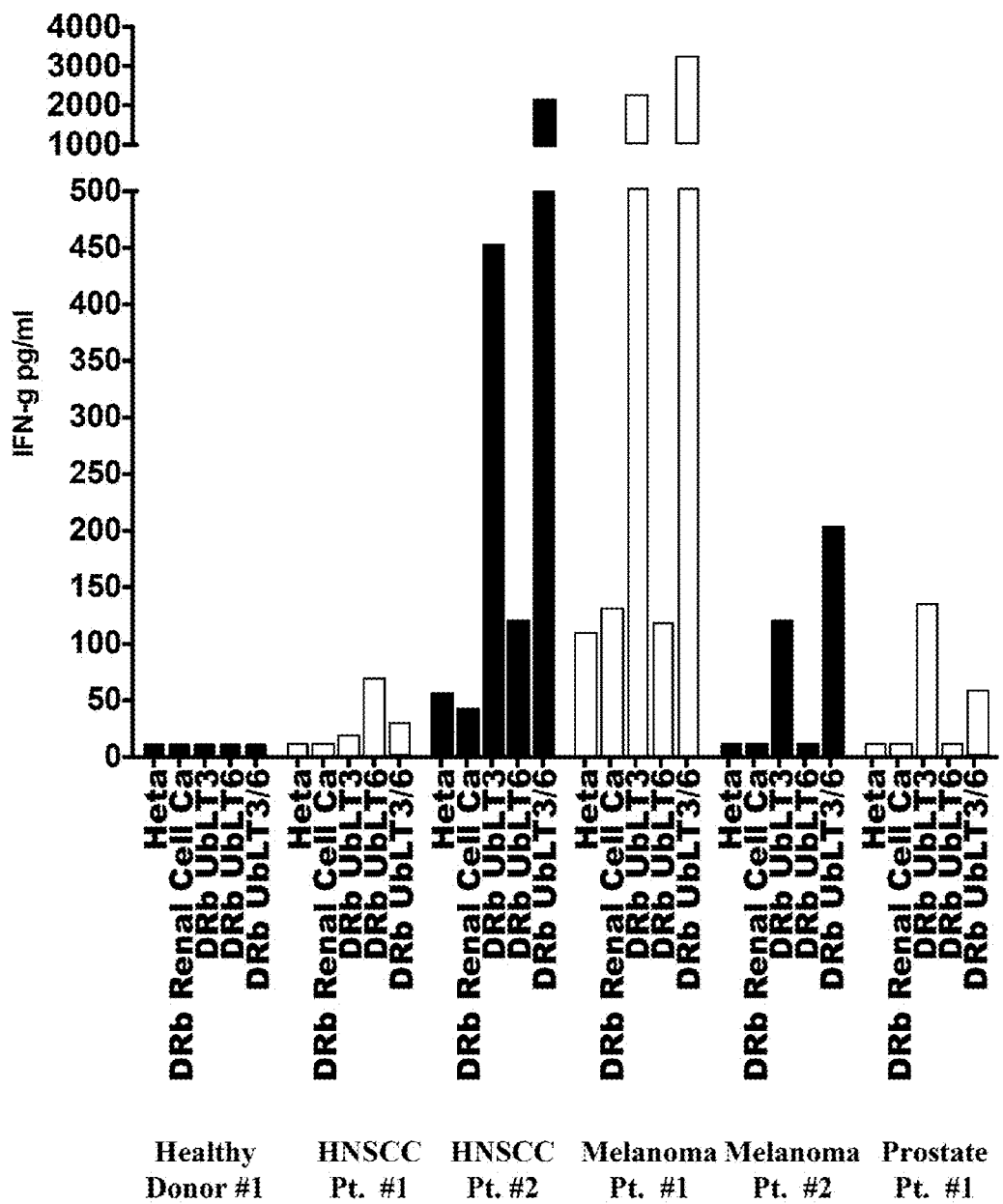
FIG. 12A is a chart demonstrating the immunomonitoring use of AAECs to detect anti-cancer immune responses in some patients following therapy.

FIG. 12A shows a chart demonstrating the therapeutic immunomonitoring use of AAECs to detect anti-cancer immune responses in some patients following therapy and documenting that tumor-draining lymph nodes contain cells that are primed by cancer and can be detected using AAECs. PBMC isolated from cancer patients were isolated and utilized in experiments assaying production of IFN-γ in response to treatment with AAECs. Increased production of IFN-γ may be beneficial to treatment with a cancer vaccine as IFN-γ is an important enhancer of immune function. IFN-γ stimulates natural killer (NK) cell activity, increases antigen presentation and causes myriad transcriptional alterations important for activating immune response. Patients with HNSCC, Melanoma, and Prostate Cancer make IFN-γ when stimulated with AAECs derived from NSCLC cells. FIG. 12A shows direct ex vivo IFN-γ production from PBMC or (lymph nodes) LNs from patients with HNSCC (n=4), Melanoma (n=4), or Prostate cancer (n=4). Cells were resuspended in complete media with 5% human albumin at 5×106/ml and exposed to UbLT3 or UbLT6 AAECs for 36-40 hr. Supernatants were analyzed by Cytokine Bead Array (BD Bioscience). Based on gene array data AAECs from a renal cell cancer patient was used as a negative control. PBMC from 2 healthy donors were tested, both were negative for IFN-γ production. AAECs does not include MHC class I molecules as measured by western blot. These findings suggest that AAECs are useful to identify the development of anti-cancer immune responses, and may be utilized as a biomarked of anti-cancer immunity.

In some embodiments, an AAEC may be derived from NSCLC. However, an AAEC may be derived from any number or variety of cancer cells or non-cancerous cells. This may include cell lines derived from: breast adenocarcinoma such as BrCA-152, MDA-MB-231, MDA-MB-361, or MDA-MB-468; Colon Carcinoma, such as HCT 116 or T84; lymphoma, such as EL4; melanoma, such as MEL-30, MEL-68, and/or MEL-40, to name a very few examples. Additionally, AAECs may be derived from syngeneic tissue, including derivation from patient tumors by methods described herein. As described above, the method to derive and administer AAECs need not be applied only to cancer vaccines and may be appropriate for developing autophagosome enriched compositions comprising bacterial, fungal, viral, or protozoan antigens.

Figure 12B:
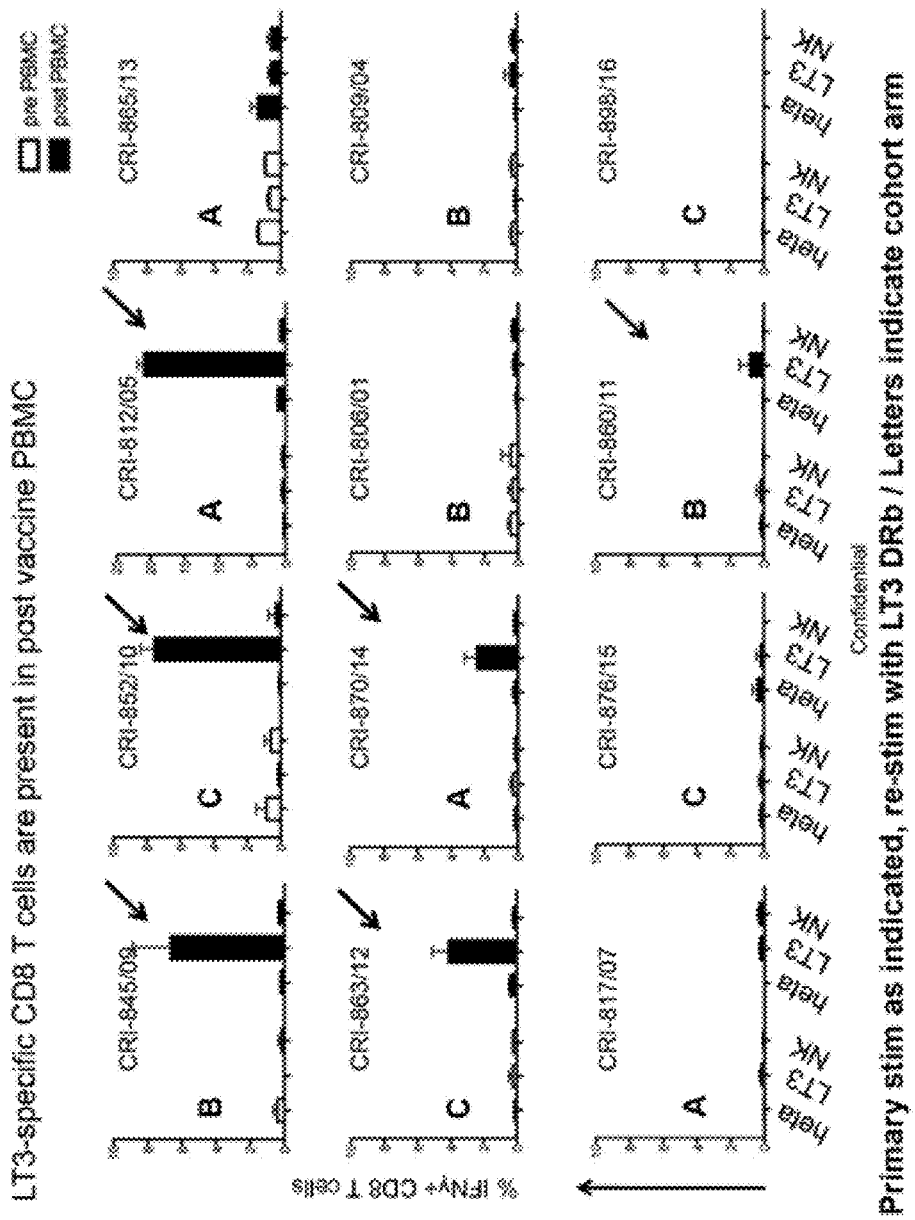
FIG. 12B is a histogram demonstrating the immunomonitoring use of AAECs to detect anti-cancer immune responses in patients following vaccination.

FIG. 12B shows an assay demonstrating that patients who developed an immune response following vaccination could be detected using AAECs. This assay describes a method for assessing the immune response against a broad panel of unknown cancer antigens which are shared by many cancers. In some examples, this assay could be utilized to assess or score the anti-cancer immune response in the blood.

Figure 12C:
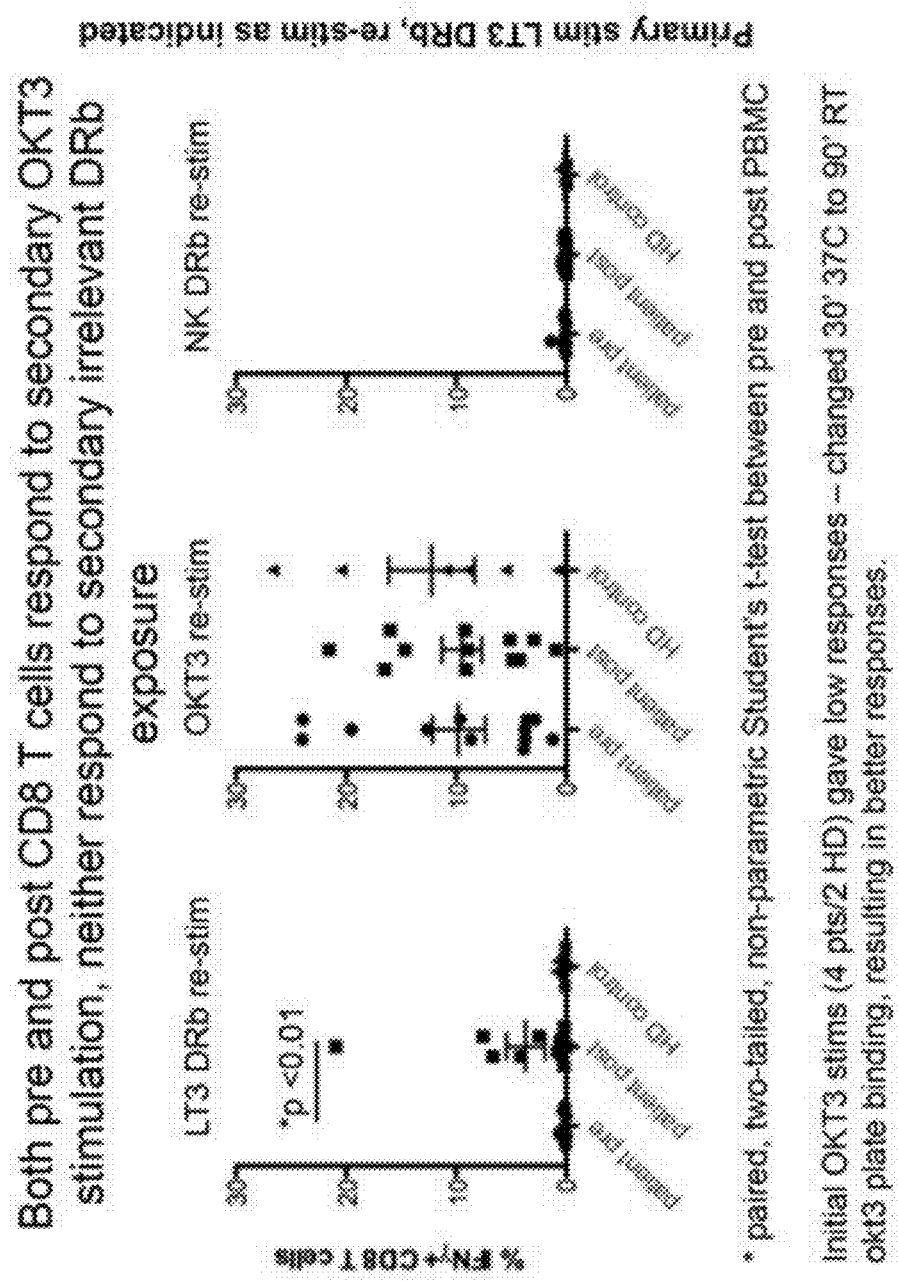
FIG. 12C is a histogram demonstrating the specificity of the immune response.

FIG. 12C further shows that immune responses in vaccinated patients could be detected using AAECs. AAECs from normal kidney were not stimulatory.

Figure 12D:
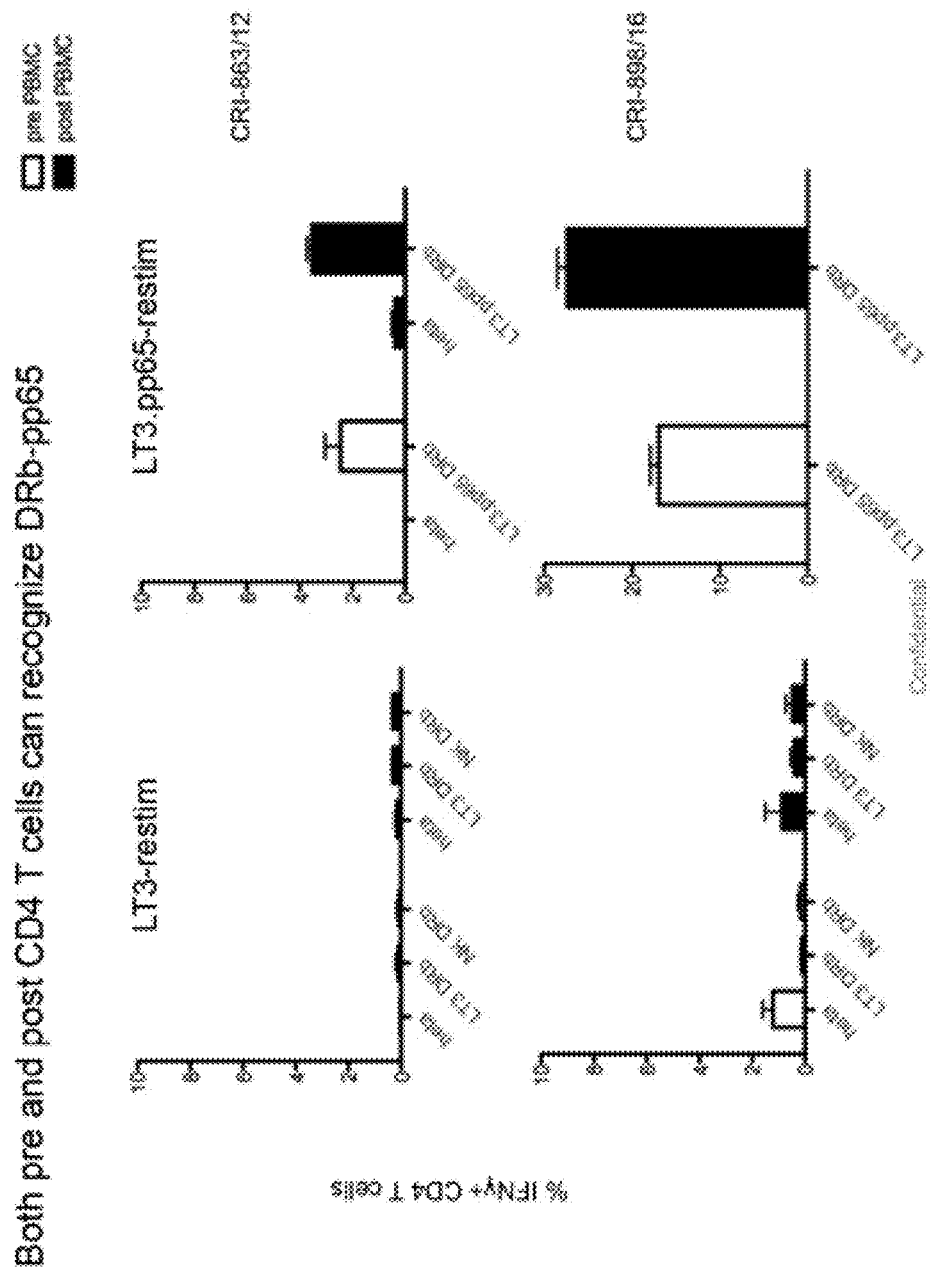
FIG. 12D is a histogram demonstrating the specificity of the immune response against pp65.

FIG. 12D is a histogram demonstrating the specificity of the immune response against pp65 and not cross-reacting with UbLT3 AAECs that do not contain the pp65 construct in a patient with immunity against CMV. AAECs were used to detect an immune response in patients who developed an immune response following vaccination. AAECs from normal kidney were not stimulatory. Immune responses were detected against pp65 in UbiLT3 (LT3.pp65DRb) Dribbles (AAECs) but not against UbLT3 AAECs (LT3DRb) or normal kidney AAECs (NK DRb).

Data from the above described experiments indicate that BDCA3 expressing monocytes may be induced in patient isolated PBMC as well as LNs. As described above, these cells may have a pro-inflammatory response which is beneficial for administration of an allogeneic autophagosome-enriched composition in a clinical setting. The pro-inflammatory response to the presence of these cells and cytokines may aid in restoration of the immune system in patients that have reduced immune function secondary to age, or prior anticancer treatments. Additionally, this pro-inflammatory response suggests a rapid expansion of the innate immune response that may be capable of targeting the specified cancer or infectious agent. This response may occur following administration of AAECs in vivo (via intra dermal, subcutaneous, intra venous, or intra nasal routes). Additionally, because of their possible pro-inflammatory activity, BDCA3+ DCs may be isolated from patient derived PBMC and used as an adjuvant for vaccination.

The data described herein and with regards to FIGS. 7-12 may enable one or more methods for inducing an immune response. In one example, a method of inducing a specific immune response in a mammal, comprising: providing a composition comprising: an enriched population of autophagosomes derived from a cell line, the enriched population of autophagosomes including: one or more toll-like receptor agonists; one or more tumor antigens; and one or more damage-associated molecular pattern molecule.

The method may further comprise: isolating peripheral blood mononuclear cells from peripheral blood of the mammal; contacting a subpopulation of the peripheral blood mononuclear cells with the enriched population of autophagosomes; and infusing the contacted peripheral blood mononuclear cells back to the mammal. The subpopulation of the peripheral blood mononuclear cells may include professional antigen presenting cells and non-professional antigen presenting cells. The peripheral blood mononuclear cells may be isolated from the mammal following the administration of GM-CSF, Flt3L, and/or CpG. The cell line has been engineered to express CD80. The cell line may have been engineered to express cytomegalovirus protein pp65. The method may further include screening for the induction of a specific immune response to the one or more tumor antigens included in the enriched population of autophagosomes by detecting the secretion of one or more cytokines specific to the one or more tumor antigens. The screening for the induction of a specific immune response may include an ELISA, ELISPOT, and/or intracellular staining assay.

Example 3

Treatment of Additional Cancers with Non-Small Lung Cancer Cell Line Derived AAEC In another example, a method similar to that described above in example 1, utilizes an allogeneic autophagosome-enriched composition derived from a cell line as a possible treatment for additional cancers as the vaccines may contain many known cancer antigens as well as immune stimulating factors.

As described herein, tumor-derived AAECs, may sequester a complex mixture of proteins including relevant cancer antigens and DAMPs. In preclinical studies, using the well-defined MCA sarcoma model where the specificity of the unique dominant tumor antigen only protects against a homologous tumor challenge it is shown that AAECs may provide cross-protection against syngeneic tumors where whole tumor cell vaccines could not (Twitty, et al. Clin Cancer Res. 2011:6467-6481). Further, AAECs, unlike the intact tumor from which they may be derived, may provide therapeutic immunity to established murine breast tumors even when derived from allogeneic tumor cells. This raises the possibility that a single NSCLC tumor cell line might be used as a vaccine for a diverse set of NSCLC histologies and possibly other cancer types. The inventors have produced AAECs from two NSCLC tumor cell lines for a Phase I/II clinical trial, UbLT3 and UbLT6. Despite their disparate gene expression profiles (8213 of 19935 genes are differentially expressed between the two cell lines), the inventors describe that UbLT3 and UbLT6 share common upregulated genes found in other cancer types.

Microarray analysis of UbLT3 and UbLT6 tumor cells before and after treatment with bortezomib and $NH_4Cl$ (two protein degradation inhibitors critical for DRibble vaccine production) were compared to normal lung tissue. Comparisons to the Cancer Genome Atlas (TCGA) datasets showed that many genes up-regulated in the vaccine cell lines are also up-regulated in other cancers (FIG. 8). In addition, western blot analysis show that at least six cancer antigens on the National Cancer Institute's (NCI's) list of prioritized cancer antigens (Cheever, et al. Clin Cancer Res. 2009:5323-5337) may be contained in AAECs (FIG. 3 A-E). While TCGA data for several cancers show similar profiles of up-regulated genes with UbLT3 and UbLT6 (HNSCC), others have few common changes in gene expression. Thus, NSCLC derived AAECs might serve as a good vaccine for patients with other cancer types. In addition to expressing relevant cancer antigens, microarray data shows several DAMPs are up-regulated (FIG. 4A). Western blots show that DAMPs including calreticulin, HMGB1, HSP70, HSP90, and Grp94 are all present in UbLT3 and UbLT6 DRibble vaccine (FIG. 4B).

It has been shown that in mice, AAECs may provide cross protection against a panel of syngeneic MCA sarcomas, while irradiated whole cell vaccine was ineffective, breaking a 50-year paradigm. Also, AAECs may provide protection when compared to whole cell vaccine in an allogeneic breast tumor model. There is evidence to support that the use of AAECs to treat a wide variety of cancers may be beneficial in terms of clinical outcomes as well as mitigating some of the negative side effects of many currently available cancer therapeutics. Experiments utilizing human cell lines have been performed that support this goal. NSCLC tumor cells lines, UbLT3 and UbLT6, share common over expressed genes with many other cancer types. These cell lines, UbLT3 and UbLT6, over expressed genes that are listed on the NCI's top cancer antigen list and genes encoding many DAMPs. Utilizing these cells lines and methods disclosed herein, autophagosome enriched-vaccines may be created. AAECs, derived from UbLT3 and UbLT6, may express at least 6 cancer antigens listed on the NCI's top cancer antigen list and at least 5 DAMPs and stimulate 5 TLR receptors. The resultant AAECs may stimulate IFN-γ production from single cell suspension of lymph nodes (LN) or PBMC cells from patients with head and neck squamous cell carcinoma (HNSCC), melanoma, and prostate, suggesting that NSCLC AAECs may stimulate IFN-γ response in a diverse set of cancers and represents a promising therapeutic for patients with these and other types of cancers.

Figure 13:
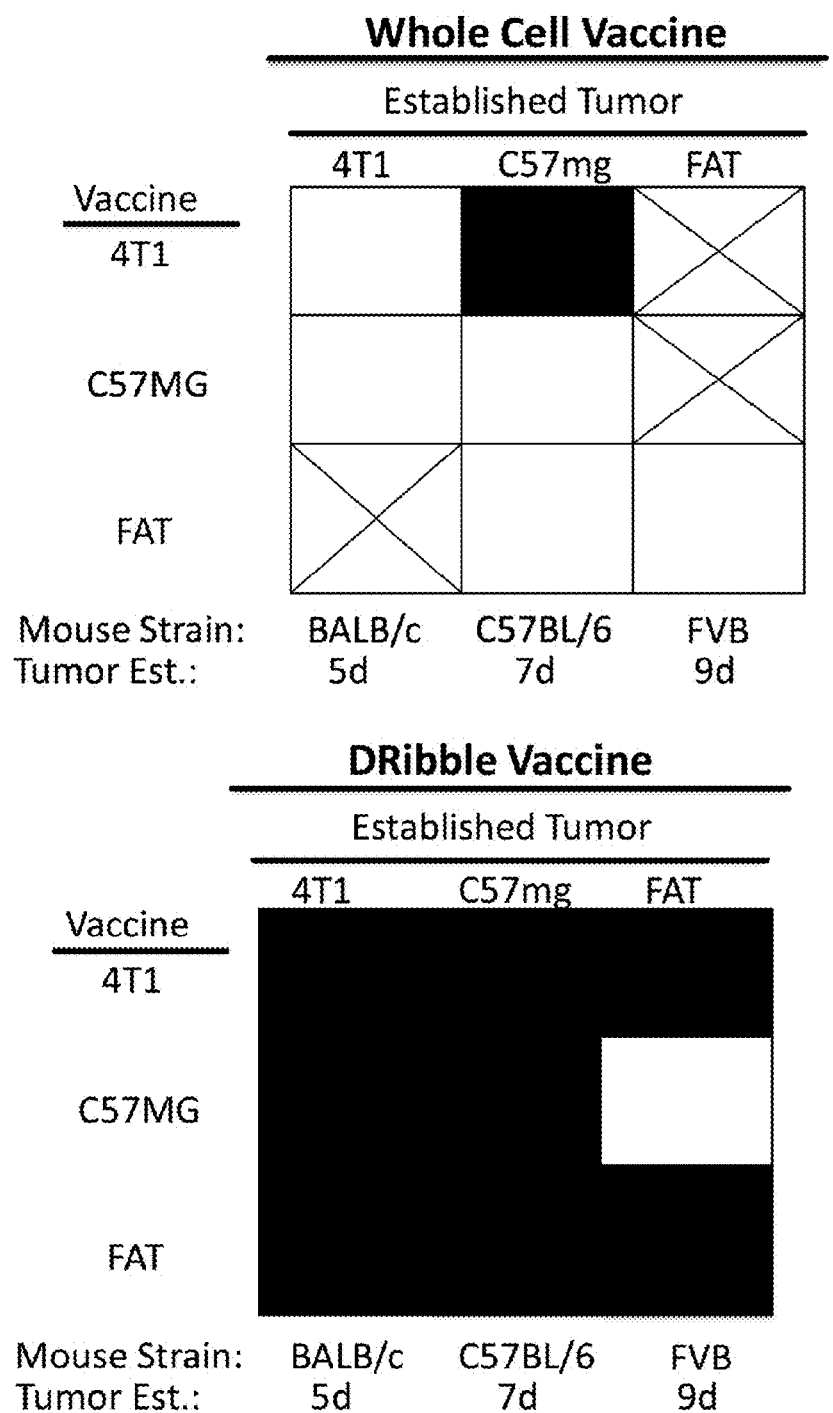
FIG. 13 is a graph that depicts induction of IFN-γ in cells from patients with various cancer types in response to AAEC treatment.

To test the therapeutic potential of an AAEC in a 5-9 established tumor model three breast tumor cell lines were utilized in three different H2 backgrounds (H2b, H2d and H2q) to test the therapeutic potential of an AAEC in a criss-cross experimental design. Whole cell vaccination with irradiated "allogeneic" or "syngeneic" tumors failed to provide significant therapeutic efficacy against 5-, 9- or 7-day established 4T1, FAT or C57MG tumors in BALB/c, FVB/n or C57BL/6 mice, respectively (data from 9 independent experiments). In contrast, immunotherapy with either the syngeneic autophagosome enriched compositions or one of the two allogeneic autophagosome enriched compositions may provide therapeutic effects in all combinations studied (p<0.05 n=15-65/group). FIG. 13 represents data from this study where the white box=no protection, "X" not done, shaded boxes=significant protection. These data provide strong support for the idea that immunotherapy that includes an allogeneic autophagosome enriched composition can provide therapeutic impact against a panel of different cancers. Specifically it supports the use of this strategy against human cancers, where there is strong evidence that the absence of an anti-cancer immune response is associated with a worse outcome (Friedman et al., Nature Reviews Cancer 2012).

Example 4

Autophagosome-Enriched Compositions May be Efficient at Membrane Protein Transfer In another example, the inventors have shown that autophagosome-enriched compositions may be efficient at membrane protein transfer, analogous to the cellular phenomenon known as "trogocytosis". Trogocytosis is a process where recipient cells acquire fragments of plasma membrane and surface molecules from donor cells. The inventors have also found that transmembrane proteins expressed by the UbLT3 and UbLT6 cell lines may be efficiently transferred to lymphocytes and monocytes in a trogocytosis-like process using AAECs derived from these cell lines. For example, AAECs may be made from MDA-CD80, UbLT3-CD80, and/or HEK293 cells via the methods described above. When these MDA-CD80, UbLT3-CD80, or HEK293 derived AAECs, which may express CD80 or other surface markers, are mixed with tumor cells or PBMC, membrane protein transfer may occur. FIGS. 14A-I demonstrate this transfer of membrane proteins, in this case CD-80. Additionally, FIGS. 14A, 14D, and 14H demonstrate that AAECs may more readily induce the transfer of CD-80 than treatment that does not contain AAECs. This transfer of CD80 to the plasma membrane of CD80 negative leukocytes was detected by flow cytometry. FIGS. 15A-E demonstrates that this transfer may be specific to AAECs and is less efficient solely in the presence of exosomes. Furthermore, FIGS. 16A-J show that the majority of CD80 expressed in the MDA-CD80 AAEC corresponds with expression of the autophagosome-specific marker LC3.

FIG. 17A summarizes some of these findings, showing that CD-80 can be transferred from AAECs to PBMCS. While transfer is most efficient to CD4+ cells and monocytes, CD80 can also be transferred to CD8+ cells and B cells with significantly more effectiveness than for control experiments. Further, FIG. 17B demonstrates that molecular transfer via AAECs is not unique to the MDA-CD80 tumor cell line, nor is the molecular transfer specific to CD80 expression. HEK-293 cells were transiently transfected to express either CD80 or CD40L. The resulting genetically engineered cells were then used to produce AAECs as described herein. As shown in FIG. 17, both HEK-293-CD80 AAECs and HEK-293-CD40L AAECs were able to efficiently transfer the expressed molecules to associated PBMCs.

This data suggests that AAECs are efficient at the transfer of membrane proteins. This may represent a phenomenon of AAECs that can be used to enable expression of immuno-modulating molecules on acceptor cells, allowing for the induction of membrane protein expression in composition recipients without requiring gene therapy or whole-cell therapy. Moreover, the data shows that this trogocytosis-like phenomenon involves proteins from the autophagosomes contained within an autophagosome-enriched composition and may suggest that autophagosome-enriched compositions may have roles in stimulating an immune response beyond just release of cytokines, antigens, or DAMPs. Further, this data shows that cells may be genetically engineered to enable the production of an effective AAEC. This may, in turn, enable a broader base of potential AAECs which target specific cancers or infectious diseases. As shown in the example herein, AAECs including CD80 may transfer the CD80 to both professional and non-professional APCs, further increasing their ability to prime and boost anti-cancer immunity. In addition to CD80, other molecules, such as CD86, CD40, CD40L, and other appropriate molecules could be engineered into the AAECs for transfer to antigen presenting cells.

The multi-faceted nature by which autophagosome-enriched compositions may induce immune response toward a target disease may make these compositions appropriate for treatment of diseases broader than cancer. Autophagosome enriched compositions, might be useful in the treatment of viral, protozoan, or bacterial infection, for example, Porcine Reproductive Respiratory Syncitial Virus (PRRSV) and malaria. In addition, these autophagosome enriched compositions may have utility beyond vaccination. The inventors describe data that suggests autophagosome enriched compositions may be capable of trogocytosing membrane proteins contained in the autophagosome onto other cells. It may be possible to exploit this property to insert membrane proteins, such as specific cellular markers onto tumor cells, or other cells, to further target specific cells.

As additional cell lines are used for the production of AAECs, the derived vaccine may be subjected to similar genetic and proteomic analysis as described above. Said analysis may determine a profile for each vaccine lot, and said profile may be compared to according profiles of known tumor cell lines (for example, as shown in FIG. 7 for UbLT3 and UbLT6) to determine which tumor types may respond to each vaccine lot. These varying vaccine lots may be derived from cancer cell lines, as well as in response to protozoan, viral, or bacterial infection.

Although the present disclosure includes specific embodiments, specific embodiments are not to be considered in a limiting sense, because numerous variations are possible. The subject matter of the present disclosure includes all novel and nonobvious combinations and subcombinations of the various elements, features, functions, and/or properties disclosed herein. The following claims particularly point out certain combinations and subcombinations regarded as novel and nonobvious. These claims may refer to "an" element or "a first" element or the equivalent thereof. Such claims should be understood to include incorporation of one or more such elements, neither requiring, nor excluding two or more such elements. Other combinations and subcombinations of features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A composition, comprising:
an enriched population of autophagosomes derived from a non-small cell lung carcinoma cell line, and wherein the enriched population of autophagosomes includes:
one or more toll-like receptor agonists;
one or more tumor antigens; and
one or more damage-associated molecular pattern molecules.

2. The composition of claim 1, wherein the one or more toll-like receptor agonists include agonists for toll-like receptor 2, toll-like receptor 3, toll-like receptor 4, toll-like receptor 7, and/or toll-like receptor 9, or a combination thereof.

3. The composition of claim 2, wherein the one or more tumor antigens include WT1, p53, Survivin, EphA2, Cyclin B1, and/or XAGE1 or a combination thereof.

4. The composition of claim 3, wherein the one or more damage-associated molecular pattern molecules include calreticulin, HMGB1, HSP70, HSP90, and/or Grp94 or a combination thereof.

5. The composition of claim 4, wherein the non-small cell lung carcinoma cell line is a UbLT3 cell line.

6. The composition of claim 4, wherein the non-small cell lung carcinoma cell line is a UbLT6 cell line.

7. The composition of claim 1, further comprising a molecule configured to augment an immune response against the one or more tumor antigens comprising the enriched population of autophagosomes.

8. The composition of claim 7, where the molecule is polyinosinic:polycytidylic acid.

9. The composition of claim 7, further comprising a non-specific adjuvant.

10. The composition of claim 9, where the non-specific adjuvant is IFN-$\gamma$.

11. A method of inducing a specific immune response in a mammal, comprising:
providing a composition comprising:
an enriched population of autophagosomes derived from a cell line, the enriched population of autophagosomes including:
one or more toll-like receptor agonists;
one or more tumor antigens; and
one or more damage-associated molecular pattern molecules;
contacting peripheral blood mononuclear cells of the mammal with the composition; and
allowing the contacted peripheral blood mononuclear cells to stimulate T-Cells of the mammal.

12. The method of claim 11, further comprising:
isolating peripheral blood mononuclear cells from peripheral blood of the mammal;
contacting a subpopulation of the isolated peripheral blood mononuclear cells with the enriched population of autophagosomes; and
infusing the contacted subpopulation of isolated peripheral blood mononuclear cells back to the mammal.

13. The method of claim 12, where the subpopulation of the isolated peripheral blood mononuclear cells include professional antigen presenting cells and non-professional antigen presenting cells.

14. The method of claim 11, where the peripheral blood mononuclear cells are isolated from the mammal following administration of GM-CSF, Flt3L, and/or CpG.

15. The method of claim 11, where the cell line has been engineered to express CD80.

16. The method of claim 11, where the cell line has been engineered to express cytomegalovirus protein pp65.

17. The method of claim 11, further comprising:
screening for an induction of a specific immune response to the one or more tumor antigens included in the enriched population of autophagosomes by detecting secretion of one or more cytokines specific to the one or more tumor antigens.

\* \* \* \* \*